US009155739B2

(12) United States Patent
Chern et al.

(10) Patent No.: US 9,155,739 B2
(45) Date of Patent: Oct. 13, 2015

(54) HISTONE DEACETYLASES (HDACS) INHIBITORS

(71) Applicant: ANNJI PHARMACEUTICAL CO., LTD., Taipei (TW)

(72) Inventors: Ji-Wang Chern, Taipei (TW); Chao-Wu Yu, Taipei (TW); Pei-Teh Chang, Taipei (TW)

(73) Assignee: ANNJI PHARMACEUTICAL CO., LTD., Taipei (TW)

( * ) Notice: Subject to any disclaimer, the term of this patent is extended or adjusted under 35 U.S.C. 154(b) by 0 days.

(21) Appl. No.: 14/666,169

(22) Filed: Mar. 23, 2015

(65) Prior Publication Data
US 2015/0196563 A1 Jul. 16, 2015

Related U.S. Application Data

(63) Continuation of application No. 13/855,525, filed on Apr. 2, 2013.

(60) Provisional application No. 61/622,127, filed on Apr. 10, 2012.

(51) Int. Cl.
*A61K 31/517* (2006.01)
*C07D 239/91* (2006.01)
*C07D 403/06* (2006.01)

(52) U.S. Cl.
CPC ............ *A61K 31/517* (2013.01); *C07D 239/91* (2013.01); *C07D 403/06* (2013.01)

(58) Field of Classification Search
CPC ... A01N 43/54; A61K 31/517; C07D 239/72; C07D 401/04
USPC ....................................... 514/266.2; 544/284
See application file for complete search history.

(56) References Cited

U.S. PATENT DOCUMENTS

2000/0052345    3/2006    Shcherbakova et al.

OTHER PUBLICATIONS

Pinedo et al. (2000).*
McMahon et al. (2000).*
Wilson A.J, et al. The DNA damage mark pH2AX differentiates the cytotoxic effects of small molecule HDAC inhibitors in ovarian cancer cells. Cancer biology & therapy 12, 484-493 (2011).
Rikiishi, H. Autophagic and apoptotic effects of HDAC inhibitors on cancer cells. Journal of biomedicine & biotechnology 2011, 830260 (2011).
Rajendran, P., Ho, E., Williams, D.E. & Dashwood, R.H. Dietary phyrochemicals, HDAC inhibition, and DNA damage/repair defects in cancer cells. Clinical epigenetics 3, 4 (2011).
Kim, H. et al. HDAC inhibitors downregulate MRP2 expression in multidrug resistaiet cancer cells; implication for chemosensitization. International journal of oncology 38, 807-812 (2011).
Huang, X., Wang, S., Lee, C.K., Yang, X. & Liu, B. HDAC inhibitor SNDX-275 enhances efficacy of trastuzumab in erbB2-overexpressing breast cancer cells and exhibits potential to overcome trastuzumab resistance. Cancer letters 307, 72-79 (2011).
Hagelkruys, A., Sawicka, A., Rennmayr, M. & Seiser, C. Hagelkruys, A., Sawicka, A., Rennmayr, M. & Seiser, C. The biology of HDAC in cancer: the nuclear and epigenetic components. Handbook of experimental pharmacology 206, 13-37 (2011).
Chou, C.W, Wu, M.S., Huang, W.C. & Chen, C.C. HDAC inhibition decreases the expression of EGFR in colorectal cancer cells. PloS one 6, e18087 (2011).
Wagner, J.M., Hackanson, B., Lubbert, M. Jung, M. Histone deacetylase (HDAC) inhibitors in recent clinical trials for cancer therapy. Clinical epigenetics 1, 117-136 (2010).
Sikandar, S. et al. The class I HDAC inhibitor MGCD0103 induces cell cycle arrest and apoptosis in colon cancer initiating cells by upregulating Dickkopf-1 and non-canonical Wnt signaling. Oncotarget 1, 596-605 (2010).
Kachhap, S.Ket al. Downregulation of homologous recombination DNA repair genes by HDAC inhibition in prostate cancer is mediated through the E2F1 transcription factor. PloS one 5, e11208 (2010).
West, O. Methods and non-cancer applications of HDAC inhibition. Current topics in medicinal chemistry 9, 226 (2009).
Wang, L.,et al. Increased expression of histone deacetylaces (HDACs) and inhibition of prostate cancer growth and invasion by HDAC inhibitor SAHA. American journal of translational research 1, 62-71 (2009).

* cited by examiner

*Primary Examiner* — Paul V Ward
(74) *Attorney, Agent, or Firm* — Hsiu-Ming Saunders; Intellectual Property Connections Inc.

(57) ABSTRACT

Histone deacetylases inhibitors (HDACIs) and methods for treating cancer in a subject in need thereof are disclosed. The HDACIs comprise a compound of Formula X.

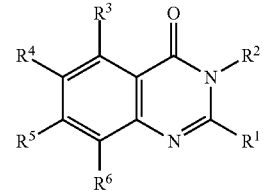

Formula X or a pharmaceutically acceptable salt thereof. In one embodiment of the invention, $R^1$ is ethyl; $R^2$ is 2-phenylethyl; $R^3$ is hydrogen; $R^4$ is fluoro; $R^5$ is (2E)-3-N-hydroxyamino-3-oxo-propenyl; and $R^6$ is hydrogen, or a salt thereof. In another embodiment of the invention, $R^1$ is ethyl; $R^2$ is 2-phenylethyl; $R^3$ is hydrogen; $R^4$ is (2E)-3-N-hydroxyamino-3-oxo-propenyl; $R^5$ is chloro or fluoro; and $R^6$ is hydrogen.

20 Claims, 1 Drawing Sheet

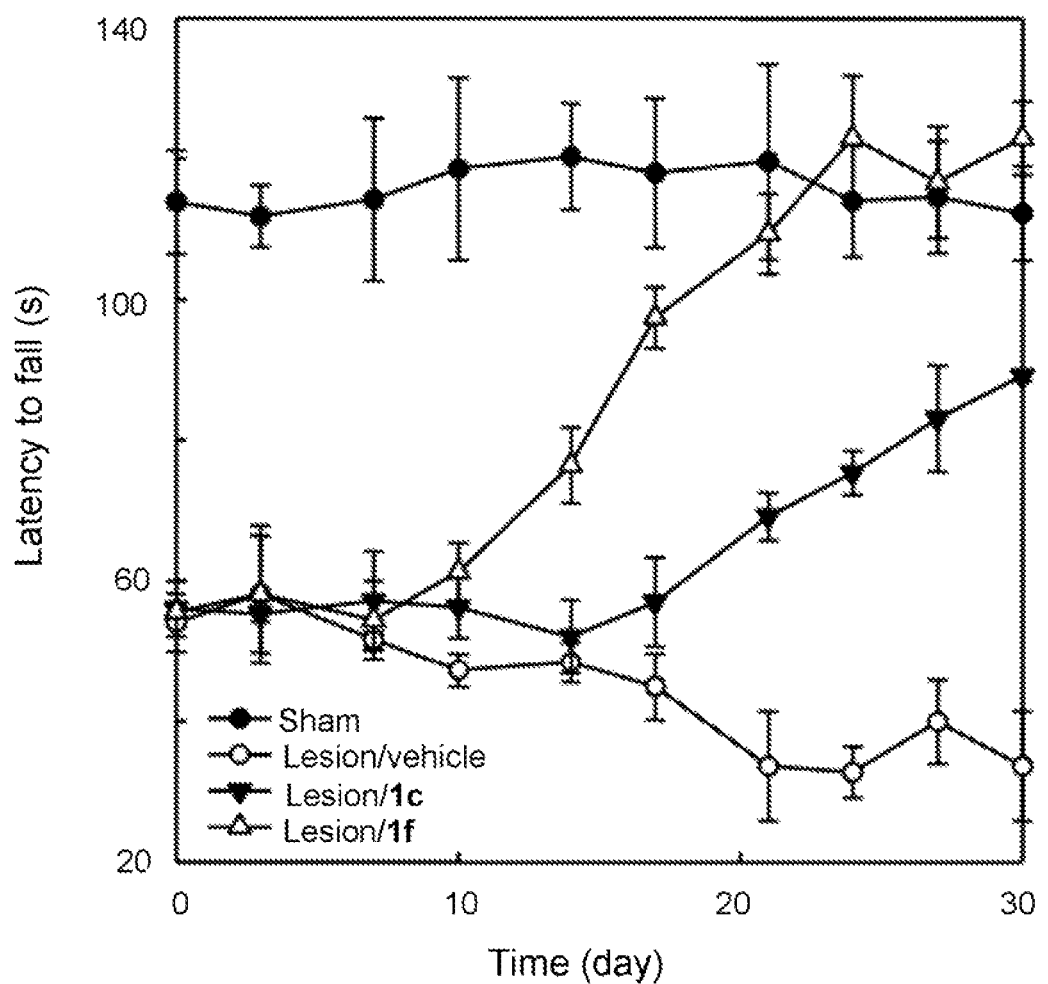

HISTONE DEACETYLASES (HDACS) INHIBITORS

REFERENCE TO RELATED APPLICATION

The present application is a Continuation application of U.S. application Ser. No. 13/855,525 filed April, 2013, which status is allowed, and claim priority to U.S. Provisional Application Ser. No. 61/622,127, filed Apr. 10, 2012, all of which are herein incorporated by reference in their entireties.

FIELD OF THE INVENTION

The present invention relates generally to histone deacetylases inhibitors.

BACKGROUND OF THE INVENTION

WO2008040934, WO2008068170, WO/2008/087514, WO/2009/026446, WO/2009/045440, WO/2011/011186, U.S. Pat. Nos. 8,188,138, 8,058,273, and 7,803,800 disclose histone deacetylases (HDACs) inhibitors having antitumor activities and antineurondegenerative activities.

SUMMARY OF THE INVENTION

In one aspect, the invention relates to a compound having the structure

Formula X or a pharmaceutically acceptable salt, a solvate or hydrate, a prodrug, or a metabolite thereof, wherein $R^1$ is hydrogen, $(C_1-C_6)$alkyl, or $(C_3-C_6)$cycloalkyl;

$R^2$ is $(C_6-C_{18})$aryl, $(C_6-C_6)$aryl$(C_1-C_6)$heteroaryl$(C_1-C_6)$alkyl, halo$(C_6-C_{18})$aryl$(C_1-C_6)$alkyl, or $(C_1-C_6)$alkoxy$(C_6-C_{18})$aryl$(C_1-C_6)$alkyl;

$R^3$ is hydrogen or N-hydroxyamino-oxo$(C_2-C_6)$alkenyl;

$R^4$ is hydrogen, halogen, N-hydroxyamino-oxo$(C_2-C_6)$alkenyl or N-hydroxyaminocarbonyl$(C_6-C_{18})$aryl$(C_1-C_6)$alkylene;

$R^5$ is hydrogen, halogen, N-hydroxyamino-oxo$(C_2-C_6)$alkenyl, N-hydroxyaminocarbonyl$(C_6-C_{18})$aryl$(C_1-C_6)$alkylene, or amino$(C_6-C_{18})$aryl-oxo$(C_2-C_6)$alkenyl; and $R^6$ is hydrogen, N-hydroxyamino-oxo$(C_2-C_6)$alkenyl, N-hydroxyamino$(C_6-C_{18})$aryl $(C_1-C_6)$alkylene or N-hydroxyaminocarbonyl$(C_6-C_{18})$aryl$(C_1-C_6)$alkylene.

In one embodiment of the invention, wherein $R^1$ is hydrogen, methyl, ethyl, cyclopropyl, or isopropyl;

$R^2$ is phenyl, benzyl, 2-phenylethyl, 3-phenylpropyl, 2-(1H-indol-3-yl)ethyl, 2-(4-fluorophenyl)ethyl, or 2-(4-methoxyphenyl)ethyl;

$R^3$ is hydrogen or (2E)-3-N-hydroxyamino-3-oxo-propenyl;

$R^4$ is hydrogen, fluoro, (2E)-3-N-hydroxyamino-3-oxo-propenyl, or 4-(N-hydroxyaminocarbonyl)benzyl;

$R^5$ is hydrogen, chloro, fluoro, (2E)-3-N-hydroxyamino-3-oxo-propenyl, 4-(N-hydroxyaminocarbonyl)benzyl or (2E)-3-N-(2-aminophenyl)-3-oxo-propenyl; and $R^6$ is hydrogen, (2E)-3-N-hydroxyamino-3-oxo-propenyl, 4-(N-hydroxyaminocarbonyl)phenyl, or 4-(N-hydroxyaminocarbonyl)benzyl, or a salt thereof.

In another embodiment of the invention, wherein $R^1$ is hydrogen, methyl, ethyl, cyclopropyl, or isopropyl;

$R^2$ is phenyl, benzyl, 2-phenylethyl, 3-phenylpropyl, 2-(1H-indol-3-yl)ethyl, 2-(4-fluorophenyl)ethyl, or 2-(4-methoxyphenyl)ethyl;

$R^3$ is hydrogen or (2E)-3-N-hydroxyamino-3-oxo-propenyl;

$R^4$ is hydrogen, (2E)-3-N-hydroxyamino-3-oxo-propenyl, or 4-(N-hydroxyaminocarbonyl)benzyl;

$R^5$ is hydrogen, (2E)-3-N-hydroxyamino-3-oxo-propenyl, 4-(N-hydroxyaminocarbonyl)benzyl, or (2E)-3-N-(2-aminophenyl)-3-oxo-propenyl; and $R^6$ is hydrogen, (2E)-3-N-hydroxyamino-3-oxo-propenyl 4-(N-hydroxyaminocarbonyl)phenyl, or 4-(N-hydroxyaminocarbonyl)benzyl, or a salt thereof.

In another embodiment of the invention, wherein $R^1$ is ethyl;

$R^2$ is 2-phenylethyl;

$R^3$ hydrogen;

$R^4$ is fluoro;

$R^5$ is (2E)-3-N-hydroxyamino-3-oxo-propenyl; and $R^6$ is hydrogen, or a salt thereof.

Further in another embodiment of the invention, wherein $R^1$ is ethyl;

$R^2$ is 2-phenylethyl;

$R^3$ is hydrogen;

$R^4$ is (2E)-3-N-hydroxyamino-3-oxo-propenyl;

$R^5$ is chloro or fluoro; and $R^6$ is hydrogen, or a salt thereof.

Further in another embodiment of the invention, the compound is selected from the group consisting of (2E)-3-(3,4-dihydro-2-methyl-4-oxo-3-phenylquinazolin-5-yl)-N-hydroxyacrylamide, (2E)-3-(3,4-dihydro-2-methyl-4-oxo-3-phenylquinazolin-6-yl)-N-hydroxyacrylamide, (2E)-3-(3,4-dihydro-2-methyl-4-oxo-3-phenylquinazolin-7-yl)-N-hydroxyacrylamide, (2E)-3-(3,4-dihydro-2-methyl-4-oxo-3-phenylquinazolin-8-yl)-N-hydroxyacrylamide, (2E)-3-(3-benzyl-3,4-dihydro-2-methyl-4-oxoquinazolin-7-yl)-N-hydroxyacrylamide, (2E)-3-(3,4-dihydro-2-methyl-4-oxo-3-phenethylquinazolin-7-yl)-N-hydroxyacrylamide, (2E)-3-(3-(2-(1H-indol-3-yl)ethyl)-3,4-dihydro-2-methyl-4-oxoquinazolin-7-yl)-N-hydroxyacrylamide, (2E)-3-(3,4-dihydro-4-oxo-3-phenethylquinazolin-7-yl)-N-hydroxyacrylamide, (2E)-3-(2-ethyl-3,4-dihydro-4-oxo-3-(phenethylquinazolin-7-yl)-N-hydroxyacrylamide, (2E)-3-(2-ethyl-3,4-dihydro-4-oxo-3-phenylpropyl)quinazolin-7-yl)-N-hydroxyacrylamide, (2E)-3-(2-cyclopropyl-3,4-dihydro-4-oxo-3-phenethylquinazolin-7-yl)-N-hydroxyacrylamide, (2E)-3-(3,4-dihydro-2-isopropyl-4-oxo-3-phenethylquinazolin-7-yl)-N-hydroxyacrylamide, (2E)-3-(3-(4-methoxyphenethyl)-2-ethyl-3,4-dihydro-4-oxoquinazolin-7-yl)-N-hydroxyacrylamide, (2E)-3-(3-(4-fluorophenethyl)-2-ethyl-3,4-dihydro-4-oxoquinazolin-7-yl)-N-hydroxyacrylamide, 4-((2-ethyl-3,4-dihydro-4-oxo-3-phenethylquinazolin-6-yl)methyl)-N-hydroxybenzamide, 4-((2-ethyl-3,4-dihydro-4-oxo-3-phenethylquinazolin-7-yl)methyl)-N-hydroxybenzamide, 4-((2-ethyl-3,4-dihydro-4-oxo-3-phenethylquinazolin-8-yl)methyl)-N-hydroxybenzamide, 4-(2-ethyl-3,4-dihydro-4-oxo-3-phenethylquinazolin-8-yl)-N-hydroxybenzamide, and (2E)-N-(2-aminophenyl)-3-(3,4-dihydro-2-methyl-4-oxo-3-phenethylquinazolin-7-yl)acrylamide.

In another embodiment of the invention, the compound is (2E)-3-(2-ethyl-6-fluoro-3,4-dihydro-4-oxo-3-phenethylquinazolin-7-yl)-N-hydroxyacrylamide, or a salt thereof.

In another embodiment of the invention, the compound is (2E)-3-(2-ethyl-7-fluoro-3,4-dihydro-4-oxo-3-phenethylquinazolin-6-yl)-N-hydroxyacrylamide, (2E)-3-(7-chloro-2-ethyl-3,4-dihydro-4-oxo-3-phenethylquinazolin-6-yl)-N-hydroxyacrylamide, or a salt thereof.

In another aspect, the invention relates to a composition comprising a therapeutically effective amount of a compound as aforementioned, or a pharmaceutically acceptable salt, a solvate or hydrate, a prodrug, or a metabolite thereof, and a pharmaceutically acceptable carrier or vehicle.

In another aspect the invention relates to a composition for use in treating a tumor disease associated with deregulation of the activity of histone deacetylases, wherein the composition comprises a therapeutically effective amount of a compound as aforementioned, or a pharmaceutically acceptable salt, a solvate or hydrate, a prodrug, or a metabolite thereof, and a pharmaceutically acceptable carrier or vehicle.

Further in another aspect, the invention relates to a composition for use in treating a tumor disease associated with deregulation of the activity of historic deacetylases as aforementioned, wherein the tumor disease is selected from the group consisting of pancreatic carcinoma, hepatocellular carcinoma, colon tumor, breast tumor, prostate tumor, lymphoma and cutaneous tumor In one embodiment of the invention, the cutaneous tumor disease is selected from melanomas and basal carcinomas.

In another aspect, the invention relates to a composition for use in treating a disease or condition wherein inhibition of HDAC provides a benefit, the composition comprising a therapeutically effective amount of a compound as aforementioned, or a pharmaceutically acceptable salt, a solvate or hydrate, a prodrug, or a metabolic thereof; and a pharmaceutically acceptable carrier or vehicle.

Further in another aspect, the invention relates to a composition for use in treating a neurodegenerative disease selected from the group consisting of Huntington's diseases (HD), Alzheimer's disease (AD), Parkinson's disease (PD), and Amyotrophic lateral sclerosis (ALS), comprising a therapeutically effective amount of a compound as aforementioned, or a pharmaceutically acceptable salt, a solvate or hydrate, a prodrug, or a metabolite thereof, and a pharmaceutically acceptable carrier or vehicle.

Further in another aspect, the invention relates to a composition for use in inhibiting the activity of histone deactylase (HDAC), the composition comprising an effective amount of a compound as aforementioned, or a pharmaceutically acceptable salt, a solvate or hydrate, a prodrug, or a metabolite thereof, and a pharmaceutically acceptable carrier or vehicle.

Yet in another aspect, the invention relates to a composition for use in treating a subject afflicted with breast cancer, colon cancer, large cell lung cancer, adenocarcinoma of the lung, small cell lung cancer, stomach cancer, liver cancer, ovary adenocarcinoma pancreas carcinoma, prostate carcinoma, promylocytic leukemia, chronic myelocytic leukemia, or acute lymphocytic leukemia, the composition comprising a therapeutically effective amount of a compound as aforementioned, or a pharmaceutically acceptable salt, a solvate or hydrate, a prodrug, or a metabolite thereof, and a pharmaceutically acceptable carrier or vehicle.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows the results of rotarod test in Alzheimer's disease animal model treated with vehicle or compounds according to one embodiment of the invention.

DETAILED DESCRIPTION OF THE INVENTION

Definitions

Unless otherwise defined, all technical and scientific terms used herein have the same mailing as commonly understood by one of ordinary skill in the art to which this invention pertains. In the case of conflict, the present document, including definitions will control.

As used herein, "around", "about;" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the singular forms "a," "an," and "the" include plural reference unless the context clearly dictates otherwise. It is further noted that the claims run be drafted to exclude any optional element. As such, this statement is intended to serve as antecedent basis for use of such exclusive terminology as "solely," "only," and the like in connection with the recitation of claim elements, or use of a "negative" limitation.

Specific and preferred values listed below for radicals, substituents, and ranges, are for illustration only; they do not exclude other defined values or other values within defined ranges for the radicals and substituents.

A dash ("-") that is not between two letters or symbols is used to indicate a point of attachment for a moiety or substituent. For example, the moiety —$CONH_2$ is attached through the carbon atom.

The term "amino" refers to —$NH_2$. The amino group can be optionally substituted as defined herein for the term "substituted."

The term "hydroxyamino" refers to —NHOH.

The term "alkyl" refers to a $C_1$-$C_{18}$ hydrocarbon containing normal, secondary, tertiary or cyclic carbon atoms. Examples are methyl, ethyl, 1-propyl, 2-propyl, 1-butyl, 2-methyl-1-propyl(iso-butyl, —$CH_2CH(CH_3)_2$), 2-butyl (sec-butyl, —$CH(CH_3)CH_2CH_3$), 2-methyl-2-propyl(tert-butyl, —$C(CH_4)_4$), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl.

The alkyl can be a monovalent hydrocarbon radical, as described and exemplified above, or it can be a divalent hydrocarbon radical (i.e., alkylene).

The term "alkenyl" refers to a $C_2$-$C_{18}$ hydrocarbon containing normal, secondary, tertiary or cyclic carbon atoms with at least one site of unsaturation, i.e., a carbon-carbon, $sp^2$ double bond. Examples include, but are not limited to: ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$). The alkenyl can be a monovalent hydrocarbon radical, as described and exemplified above, or it can be a divalent hydrocarbon radical (i.e., alkenylene).

The term "alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to methylene (—CH$_2$—) 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and the like.

The term "alkoxy" refers to the group alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like. The aryl can optionally be a divalent radical, thereby providing an arylene.

The aryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfinamoyl, sulfino, sulfo, sulfoamino, thiosulfo, NR$^x$R$^y$ and/or COOR$^x$, wherein each and R$^x$ and R$^y$ are independently H, alkyl, alkenyl, aryl, heteroaryl, heterocycle, cycloalky, or hydroxy.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The term "carboxyl" refers to —COOH.

The phrase "compounds of the disclosure" refer to compounds of Formula (X) and pharmaceutically acceptable enantiomers, diastereomers, and salts thereof. Similarly, references to intermediates, are meant to embrace their salts where the context so permits.

The "compound" refers to a chemical combination of two or more elements that may have an impact on any living system such as a cell, nerve or tissue.

The term "cycloalkyl" refers to gate alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkenyl, alkoxy, halo, haloalkyl, hydroxy, hydroxyalkyl aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy. As used herein, the terms "halogen" or "halo" refer to fluoro, chloro, bromo, and iodo. Similarly, the term "halogen" refers to fluorine, chlorine, bromine, and iodine.

As used herein, the term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted. The heteroaryl can optionally be a divalent radical, thereby providing a heteroarylene.

Examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl, or benzyl. In another embodiment heteroaryl denotes an ortho-fused bicyclic heterocycle of about eight to ten ring atoms derived therefrom particularly a benz-derivative or one derived by fusing a propylene, or tetramethylene diradical thereto. The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfinamoyl, sulfino, sulflo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy.

The term "hydrate" refers to the complex where the solvent is water.

The term "metabolite" refers to any compound of the Formula (X) produced in vivo or in vitro from the parent drug, or its prodrugs.

The term "oxo" refers to =O.

The pharmaceutically acceptable salts of the compounds described herein can be synthesized from the parent compound, which contains a basic or acidic moiety, by conventional chemical methods. Such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of many suitable salts are found in Remington: The Science and Practice of Pharmacy, 21$^{st}$ edition, Lippincott, Williams & Wilkins, (2005).

The term "prodrug" refers to any pharmaceutically acceptable form of compound of the Formula (X), which, upon administration to a patient, provides a compound of the Formula (X). Pharmaceutically acceptable prodrugs refer to a compound that is metabolized, for example hydrolyzed or oxidized, in the host to form a compound of the Formula (X). Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphotylated, dephosphorvlated to produce the active compound.

The prodrug can be readily prepared from the compounds of Formula (X) using methods known in the art. See, e.g. See Notari, R. E., "Theory and Practice of Prodrug Kinetics," Methods in Enzymology, 112:309 323 (1985); Bodor, N. "Novel Approaches in Prodrug Design," Drugs of the Future, 6(3):1165 182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985); Burger's Medicinal Chemistry and Drug Chemistry, Fifth Ed., Vol. 1, pp. 172 178, 949 982 (1995).

The term "solvate" refers to a complex of variable stoichiometry formed by a solute (in this invention, a compound of Formula X, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid.

The term "substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, acyloxy, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy. When a substituent is oxo (i.e., =O) or thioxo (i.e., =S) group, then two hydrogens on the atom are replaced.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water.

Methods of Making the Compounds of Formula (X)

The compounds described herein can be prepared by any of the applicable techniques of organic synthesis. Many such techniques are well known in the art. See e.g., "Compendium of Organic Synthetic Methods" (John Wiley K. Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980). Exemplary methods of making the compounds described herein are described herein in the examples below.

Numerous modifications and variations of the presently disclosed subject matter are possible in light of the above teachings. It is to be understood that within the scope of the claims, the disclosed subject matter May be practiced otherwise than as specifically described herein. Specific ranges, values, and embodiments provided herein are for illustration purposes only and do not otherwise limit the scope of the disclosed subject matter, as defined by the claims. The starting materials useful to synthesize the compounds of the present disclosure are known to those skilled in the art and can be readily manufactured or are commercially available.

The following methods set forth below are provided for illustrative purposes and are not intended to hunt the scope of the claimed disclosure. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

Synthesis

The compounds of the general formula X are prepared by the following procedures of schemes:

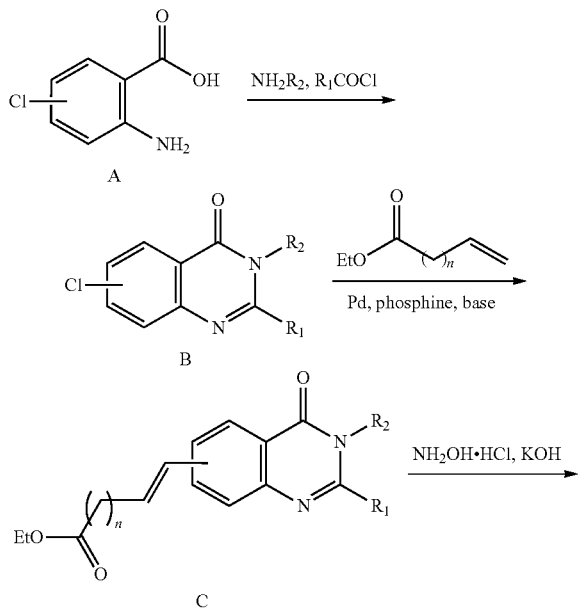

Scheme 1

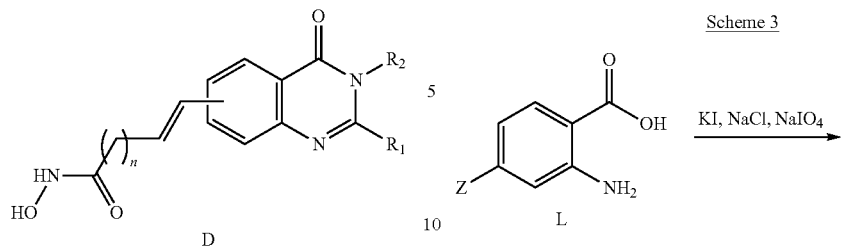
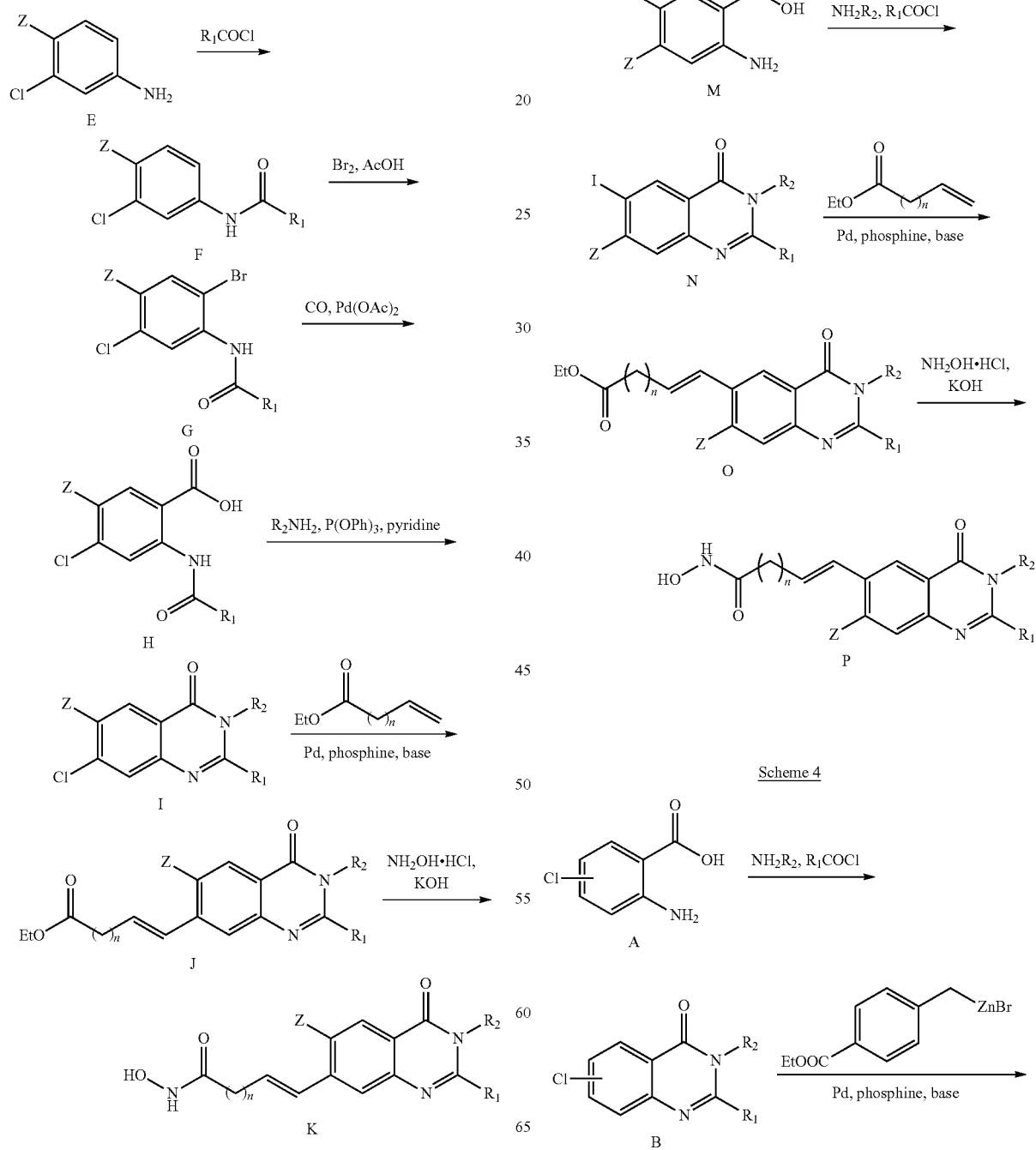

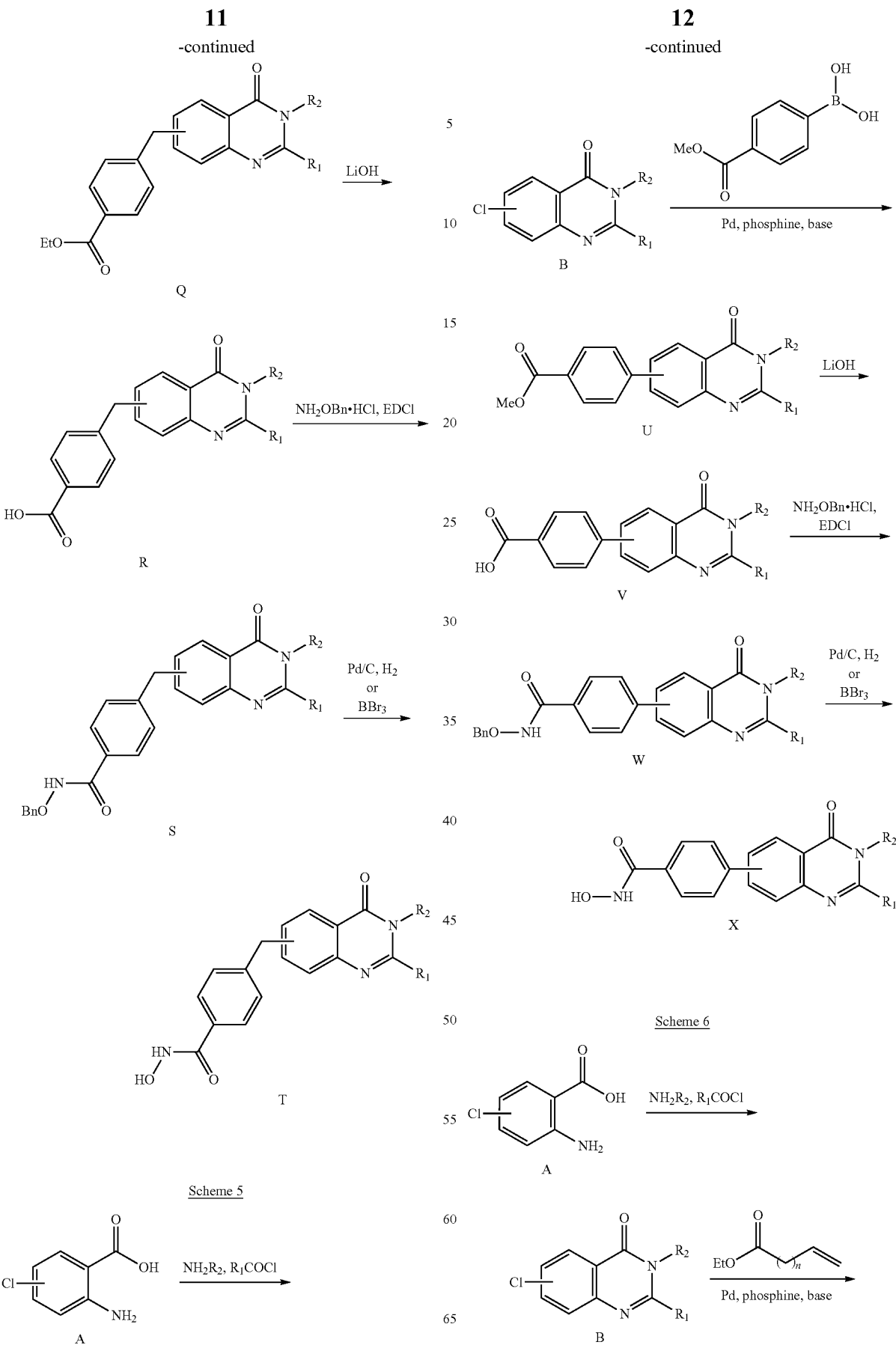

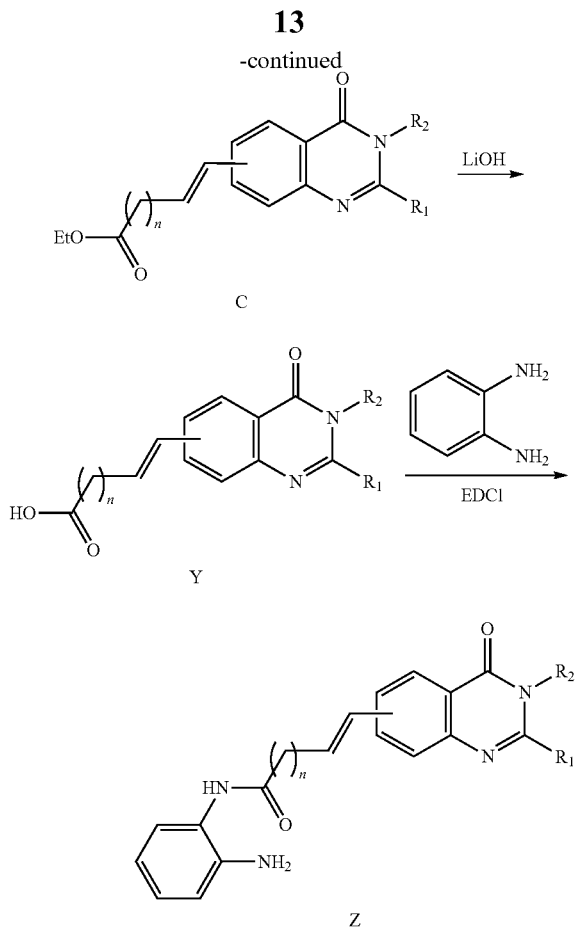

C

Y

Z

EXAMPLE 1

Preparation of N-Hydroxy-3-(2-methyl-4-oxo-3-phenyl-3,4-dihydro-quinazolin-6-yl)-acrylamide (Compound 1b)

Step 1: Preparation of 6-chloro-2-methyl-3-phenylquinazolin-4(3H)-one

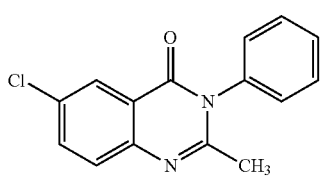 [SMILES: Cc1nc2ccc(Cl)cc2c(=O)n1-c1ccccc1]

5-chloroanthranilic acid (6 g, 34.27 mmol) mixed with triphenyl phosphite (11.1 mL, 41.08 mmol) in pyridine (25 mL) was added with acetyl chloride (3.7 mL, 51.33 mmol) and stirred at rt for 3 h. The resulting mixture was added with aniline (4.7 mL, 51.47 mmol) and irradiated with microwave at 140° C. for 10 min. The reaction mixture was then diluted with ethyl acetate (50 mL) and washed with water (3×50 mL). The organic solution was kept at rt to get solid formed, and the solution was filtered to get target compound as a white solid (5.32 g, 57.3%), $^1$H NMR (400 MHz, DMSO-$d_6$) δ 2.10 (s, 3H), 7.43-7.45 (m, 2H), 7.51-7.58 (m, 3H), 7.66 (d, J=8.8 Hz, 1H), 7.83 (dd, J=8.8, 0.4 Hz, 1H), 7.98 (d, J=2.4 Hz, 1H); $^{13}$C NMR (100 MHz, DMSO-$d_6$) δ 24.0, 121.7, 125.1, 128.2, 128.8, 129.0, 129.5, 130.5, 134.5, 137.5, 145.9, 155.0, 160.3;

Step 2: Preparation of (2E)-ethyl 3-(3,4-dihydro-2-methyl-4-oxo-3-phenylquinazolin-6-yl)acrylate

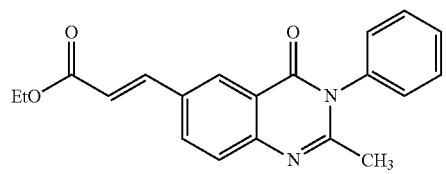 [SMILES: CCOC(=O)/C=C/c1ccc2nc(C)n(-c3ccccc3)c(=O)c2c1]

The target solid of step 1 (4 g, 14.78 mmol), Herrmann's palladacycle (0.277 g, 0.30 mmol), and [(t-Bu)$_3$Ph]BF$_4$ (0.171 g, 0.60 mmol) mixed in DMF (40 mL) was added with ethyl acrylate (1.58 mL, 14.76 mmol) and Cy$_2$NMe (3.27 mL, 14.78 mmol) and irradiated with microwave at 150° C. for 30 min (two times). The resulting mixture was evaporated to get dark green residue. The residue was suspended in ethyl acetate (50 mL) and washed with water (3×50 mL). The organic layer dried over MgSO$_4$ was evaporated to get crude yellow solid of target compound of step 2. The yellow solid was put to step 3 without further purification.

Step 3: Preparation of (2E)-3-(3,4-dihydro-2-methyl-4-oxo-3-phenylquinazolin-6-yl)-N-hydroxyacrylamide (Compound 1b)

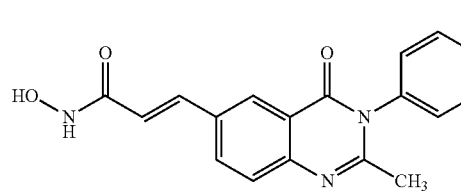

1b

NH$_2$OH.HCl (20.54 g 69.49 mmol) suspended in methanol (28 mL) was added with solution of KOH (16.59 g, 295.67 mmol) dissolved in methanol (60 mL), and the mixed solution was filtered and added dropwise for 20 min to solution of the yellow solid from step 2 suspended in methanol (40 mL) under ice bath. Then the reaction mixture was stirred from ice bath to rt for 5 h. The resulting solution was poured to ice water (300 mL) and neutralized with 3N HCl (40 mL) to get solid formed. Then the solution was filtered to get yellow solid. The solid was purified by column chromatography eluting with 5% MeOH in CH$_2$Cl$_2$ to get compound 1b as white solid (1.42 g, 29.9%); mp 173-175° C. (dec); $^1$H NMR (400 MHz, DMSO-$d_6$) δ 2.11 (s, 3H), 6.57 (d, J=15.6 Hz), 7.44-7.60 (m, 6H), 7.66 (d, J=8.4 Hz, 1H), 8.00 (dd, J=8.4, 1.6 Hz, 1H), 8.22 (d, J=1.6 Hz, 1H), 9.12 (br s, 1H), 10.79 (br s, 1H); $^{13}$C NMR (100 MHz, DMSO-$d_6$) δ 24.1, 120.0, 120.7, 125.0, 127.3, 128.4, 129.0, 129.6, 132.9, 133.3, 137.0, 137.7, 147.9, 155.2, 161.1, 162.4; ESIMS(−) m/z 320.0 [M−1]⁻; Anal. (C$_{18}$H$_{15}$N$_3$O$_3$·0.6H$_2$O) C, H, N. Calcd: 65.09, 4.92, 12.65. Found: 65.13, 5.01, 12.33.

EXAMPLE 2

Preparation of (2E)-3-(2-ethyl-6-fluoro-3,4-dihydro-4-oxo-3-phenethylquinazolin-7-yl)-N-hydroxyacrylamide (Compound 2a)

Step 1: Preparation of N-(3-chloro-4-fluorophenyl)propionamide

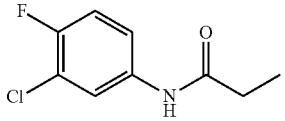

3-chloro-4-fluoroaniline (10 g, 67.32 mmol) dissolved in CH$_2$Cl$_2$ was added with propionyl chloride (6.6 mL, 74.10 mmol) and triethyl amine (10.2 mL, 73.58 mmol) dropwise under water bath, and the mixture was stirred for 2 h. The resulting solution was washed with water (2×50 mL) and saturated aqueous NaHCO$_3$ solution (12 mL). The CH$_2$Cl$_2$ layer dried over MgSO$_4$ was evaporated to give title compound as light purple solid (13.01 g, 96.3%). ¹H NMR (400 MHz, DMSO-d$_6$) δ 1.06 (t, J=7.6 Hz, 3H), 2.30 (q, 7.6 Hz, 2H) 7.31 (dd, J=9.2 and 8.8 Hz, 1H), 7.44 (ddd, J=8.8 and 4 and 2.8 Hz, 1H), 7.91 (dd, J=7.2 and 2.8 Hz, 1H), 10.04 (br s, 1H); ¹³C NMR (100 MHz, DMSO-d$_6$) δ 9.4, 29.4, 116.6, 116.8, 118.8, 119.0, 119.1, 120.2, 136.55, 136.58, 151.5, 153.9, 172.1;

Step Preparation of N-(2-bromo-5-chloro-4-fluorophenyl)propionamide

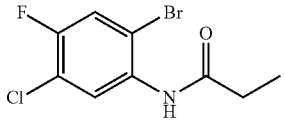

The solid (10 g, 49.60 mmol) from step 1 dissolved in acetic acid (70 mL) was added with Br$_2$ (12.7 mL, 247.93 mmol) dropwise for 2 h. Then the reaction mixture was kept stirring at rt for 5.5 h. The resulting mixture was poured to ice water (1 L) and quenched with excess of NaHSO$_3$ until the solution became clear with yellow suspension. The quenched solution was filtered to get title compound (13.52 g, 97.2%). ¹H NMR (400 MHz, DMSO-d$_6$) δ 1.07 (t, J=7.6 Hz, 3H), 2.36 (q, J=7.6 Hz, 2H), 7.80 (d, J=7.6 Hz, 1H), 7.84 (d, J=8.8 Hz, 1H), 9.50 (br s, 1H); ¹³C NMR (100 MHz, DMSO-d$_6$) δ 10.1, 29.3, 117.3, 117.4, 119.0, 119.2, 121.0, 121.2, 128.4, 134.45, 134.49, 153.4, 155.9, 173.0;

Step 3: Preparation of 4-chloro-5-fluoro-2-(propionamido)benzoic acid

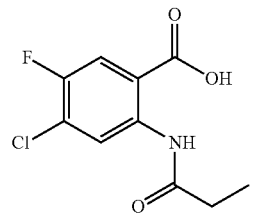 [SMILES: CCC(=O)Nc1cc(Cl)c(F)cc1C(=O)O]

The solid (10 g, 35.65 mmol) from step 2 was mixed with Pd(OAc)$_2$ (0.288 g, 1.28 mmol) and Xantphos (0.758 g, 1.28 mmol) in toluene (50 mL) and triethyl amine (26.7 mL, 192.61 mmol) under Ar. The reaction vessel was evacuated and followed by charging with CO to 1 atm. This cycle was repeated three times, and the solution was purged with CO gas for one minute. The reaction mixture was stirred at 80° C. for 24 h. The resulting mixture was injected with water (1 mL) and cooled to rt. The solution was diluted with ethyl acetate (100 mL) and filtered by celite. The filtered solution was extracted with a saturated aqueous NAHCO$_3$ solution (2×25 mL). The aqueous NaHCO$_3$ solution was acidified with 3 N HCl to pH4 and filtered to get crude solid title compound (4.06 g). The solid was put to step 4 without further purification.

Step 4: Preparation of 7-chloro-2-ethyl-6-fluoro-3-phenethylquinazolin-4(3H)-one

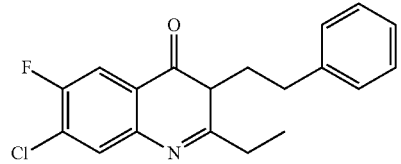 [SMILES: CCC1=Nc2cc(Cl)c(F)cc2C(=O)C1CCc1ccccc1]

The crude solid (3 g) from step 3 above mixed with triphenyl phosphite (4 mL, 14.81 mmol) in pyridine (15 mL) was stirred at rt for 4 h. The mixture was added with phenethylamine (1.55 mL, 12.18 mmol), irradiated with microwave 250 W to refluxing for 15 min. The mixture was diluted with ethyl acetate (50 mL), washed with water (2×50 mL). The ethyl acetated solution was mixed with water (50 mL) and kept at rt to give solid form. The solution was filtered to give yellow solid title compound (1.1 g, 27.2%). mp=150-152° C. (recrystallized from ethyl acetate); ¹H NMR (400 MHz, DMSO-d$_6$) δ 1.19 (t, J=7.2 Hz, 3H, CH$_3$), 2.76 (q, J=7.2 Hz, 2H, CH$_2$), 2.93 (br t, J=7.6 Hz, 2H, CH$_2$), 4.19 (br t, J=7.6 Hz, 2H, CH$_2$), 7.20-7.31 (m, 5H, ArH), 7.80 (d, J=6.4 Hz, 1H, ArH), 7.91 (d, J=8.8 Hz, 1H, ArH); ¹³C NMR (100 MHz, DMSO-d$_6$) δ 10.6, 26.9, 33.5, 44.8, 112.2, 112.4, 119.8, 119.9, 126.6, 126.8, 127.0, 128.5, 128.7, 128.8, 138.0, 144.1, 153.6, 156.1, 158.9, 160.0; Anal. (C$_{18}$H$_{16}$ClFN$_2$O) C, H, N. Calcd: 65.36, 4.88, 8.47. Found: 65.09, 4.77, 8.50.

Step 5: Preparation of (2E)-ethyl 3-(2-ethyl-6-fluoro-3,4-dihydro-4-oxo-3-phenethylquinazolin-7-yl)acrylate

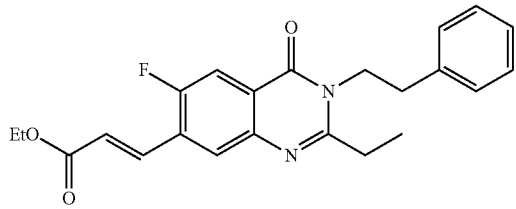 [SMILES: CCOC(=O)/C=C/c1cc2nc(CC)n(CCc3ccccc3)c(=O)c2cc1F]

The title compound was prepared using the procedure described in step 2 of example 1. Yield 69.8%; $R_f$=0.28 (EA/Hexane=1:3); mp=140-142° C. (recrystallized from ethyl acetate/hexane); $^1$H NMR (400 MHz, CDCl$_3$) δ 1.30 (t, J=7.2 Hz, 3H, CH$_3$) 1.33 (t, J=7.2 Hz, 3H, CH$_3$), 2.66 (q, J=7.2 Hz, 2H$_2$) 3.00 (br t, J=7.6 Hz, 2H, CH$_2$), 4.24-4.30 (m, 4H, 2CH$_2$), 6.67 (d, J=16.4 Hz, 1H, C=CH), 7.19-7.30 (m, 5H, ArH), 7.82 (d, J=16.4 Hz, 1H, C=CH), 7.82 (d, J=6.8 Hz, 1H, ArH), 7.90 (d, J=10.4 Hz, 1H, ArH); $^{13}$C NMR (100 MHz, CDCl$_3$) δ 11.3, 14.4, 28.1, 34.8, 45.6, 61.0, 112.3, 112.5, 122.3, 122.4, 123.9, 124.0, 127.1, 128.26, 128.29, 128.91, 128.97, 129.4, 129.6, 136.24, 136.27, 137.8, 144.02, 144.04, 157.60, 157.68, 160.2, 161.1, 161.2, 166.4; Anal. (C$_{23}$H$_{23}$FN$_2$O$_3$) C, H, N. Calcd: 70.04, 5.88, 7.10 Found: 70.02, 5.85, 7.10.

Step 6: Preparation of (2E)-3-(2-ethyl-6-fluoro-3,4-dihydro-4-oxo-3-phenethylquinazolin-7-yl)-N-hydroxyacrylamide (Compound 2a)

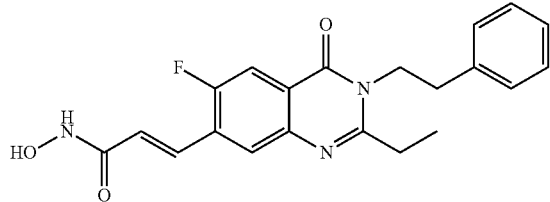

The title compound was prepared using the procedure described in step 3 of example 1. Yield 45.5%; $R_f$=0.24 (MeOH/CHCl$_3$=1:9); mp=219-221° C. (dec); $^1$H NMR (400 MHz, DMSO-d$_6$) δ 1.20 (t, J=7.2 Hz, 3H), 2.76 (q, J=7.2 Hz, 2H), 2.94 (dd, J=7.6 Hz, 2H), 4.20 (dd, J=7.6 Hz, 2H), 6.77 (d, J=16 Hz, 1H), 7.21-7.32 (m, 5H), 7.55 (d, J=16 Hz, 1H), 7.80 (d, J=6.8 Hz, 1H), 7.84 (d, J=6.4 Hz, 1H), 9.21 (br s, 1H), 10.91 (br s, 1H); $^{13}$C NMR (100 MHz, DMSO-d$_6$) δ 10.6, 26.8, 33.5, 44.7, 111.5 (d, J=24.0 Hz), 120.9 (d, J=9.0 Hz), 125.2 (d, J=6.0 Hz), 126.5, 127.9 (br s), 128.5, 128.7, 129.4 (d, J=15.0 Hz), 129.8, 138.1, 143.6, 157.8 (d, J=248.0 Hz), 157.9, 159.0, 160.0, 160.1, 161.8; ESIMS(-) m/z: 380.0 [M-1]$^-$. Anal. (C$_{21}$H$_{20}$FN$_3$O$_3$·1/10 H$_2$O) C, H, N. Calcd: 65.82, 5.31, 10.97. Found: 65.50, 5.29, 10.75.

EXAMPLE 3

Preparation of (2E)-3-(2-ethyl-7-fluoro-3,4-dihydro-4-oxo-3-phenethylquinazolin-6-yl)-N-hydroxyacrylamide (3a)

Step 1: Preparation of 2-amino-4-fluoro-5-iodobenzoic acid

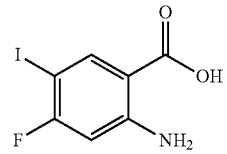 [SMILES: Nc1cc(F)c(I)cc1C(=O)O]

4-fluoroanthranilic acid (1 g, 6.32 mmol) mixed with NaIO$_4$ (1.35 g, 6.31 mmol) and NaCl (0.74 g, 12.66 mmol) in acetic acid (18 mL) was added dropwise with KI (1.05 g, 6.33 mmol) dissolved in water (2 mL) for 5 min. The reaction mixture was kept stirring at rt for 8.5 h. The product mixture was poured on 100 mL of ice water and quenched with excess of NaHSO$_3$ until the solution became clear with suspension. The solution was filtered, washed with water (200 mL) to give brown solid (1.17 g, 65.9%), $^1$H NMR (400 MHz, DMSO-d$_6$) δ 6.60 (d, J=10.8 Hz, 1H, ArH), 8.01 (d, J=7.2 Hz, 1H, ArH); $^{13}$C NMR (100 MHz, DMSO-d$_6$) δ 62.1, 62.3, 101.9, 102.1, 109.2, 141.7, 141.8, 153.3, 153.4, 162.6, 165.1, 167.6.

Step 2: Preparation of 2-ethyl-7-fluoro-6-iodo-3-phenethylquinazolin-4(3H)-one

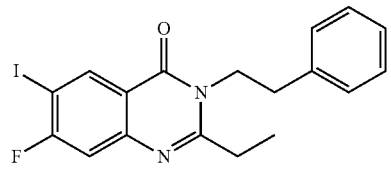 [SMILES: CCc1nc2cc(F)c(I)cc2c(=O)n1CCc1ccccc1]

The title compound was prepared using the procedure described in step 1 of example 1. Yield 81.8%; $R_f$=0.57 (EA/Hexane=1:2); $^1$H NMR (400 MHz, CDCl$_3$) δ 1.23 (t, J=7.2 Hz, 3H, CH$_3$), 2.58 (q, J=7.2 Hz, 2H, CH$_2$), 2.94 (br t, J=7.6 Hz, 2H, CH$_2$), 4.20 (br t, J=7.6 Hz, 2H, CH$_2$), 7.13-7.26 (m, 6H, ArH), 8.62 (d, J=6.8 Hz, 1H, ArH); $^{13}$C NMR (100 MHz, CDCl$_3$) δ 10.1, 27.2, 33.6, 44.5, 78.4, 78.7, 111.3, 111.5, 117.7, 117.8, 125.9, 127.7, 127.8, 136.6, 137.41, 137.45, 148.1, 148.2, 158.5, 159.1, 162.4, 164.9.

Step 3: Preparation of (2E)-ethyl 3-(2-ethyl-7-fluoro-3,4-hydro-4-oxo-3-phenethylquinazolin-6-yl)acrylate

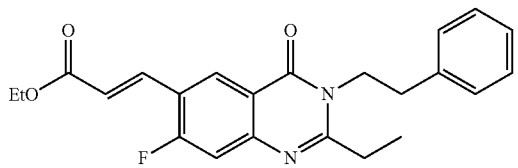 [SMILES: CCOC(=O)/C=C/c1cc2c(=O)n(CCc3ccccc3)c(CC)nc2cc1F]

Step 4: Preparation of (2E)-3-(2-ethyl-7-fluoro-3,4-dihydro-4-oxo-3-phenethylquinazolin-6-yl)-N-hydroxyacrylamide (3a)

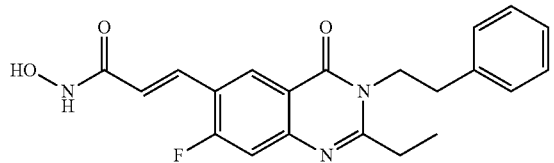

3a

The title compound was prepared from the oil residue of step 3 using the similar procedure described above of the step 3 of example 1 to give compound 3a as red solid (36.7%, step 2 and step 3); $R_f$=0.42(MeOH/CHCl$_3$=1:9); mp=183-185° C. (dec) (recrystallized from methanol); $^1$H NMR (400 MHz, DMSO-d$_6$) δ 1.19 (t, J=6.0 Hz, 3H), 2.76 (m, 2H), 2.94 (m, 2H), 4.20 (m, 2H), 6.65 (d, J=16 Hz, 1H), 7.21-7.32 (m, 5H), 7.39 (d, J=12.0 Hz, 1H), 7.54 (d, J=16 Hz, 1H), 8.31 (d, J=8.4 Hz, 1H), 9.17 (br s, 1H), 10.87 (br s, 1H); $^{13}$C NMR (100 MHz, DMSO-d$_6$) δ 10.6, 27.1, 33.5, 44.6, 112.4 (d, J=22.0 Hz), 117.1, 121.9 (d, J=14.0 Hz), 122.7 (d, J=6.0 Hz), 126.6, 127.4 (d, J=5.0 Hz), 128.5, 128.7, 129.7, 138.1, 148.9 (d, J=14.0 Hz), 160.0, 160.2, 162.0, 163.5 (d, J=255.0 Hz); ESIMS(−) m/z 380.0 [M−1]$^−$. Anal. (C$_{21}$H$_{20}$FN$_3$O$_3$) C, H, N. Calcd: 66.13, 5.29, 11.02. Found: 66.05, 5.15, 10.76.

EXAMPLE 4

Preparation of 4-((2-ethyl-3,4-dihydro-4-oxo-3-phenethylquinazolin-8-yl)methyl)-N-hydroxybenzamide (Compound 4c)

Step 1: Preparation of 8-chloro-2-ethyl-3-phenethylquinazolin-4(3H)-one

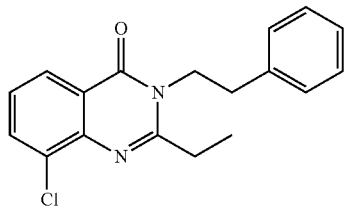 [SMILES: CCc1nc2c(Cl)cccc2c(=O)n1CCc1ccccc1]

The title compound was prepared using the procedure described above of the step 1 of example 1 from 3-chloroanthranilic acid (5 g, 29.14 mmol) to give white needle crystal (4.3 g, 47.2%), $R_f$=0.53 (EA/Hexane=1:2); $^1$H NMR (400 MHz, DMSO-d$_6$) δ 1.24 (t, J=7.2 Hz, 3H), 2.79 (q, J=7.2 Hz, 2H), 2.94 (t, J=7.6 Hz, 2H), 4.20 (t, J=7.6 Hz, 2H), 7.20-7.31 (m, 5H), 7.41 (dd, J=8.0, 7.6 Hz, 1H), 7.89 (d, J=17.6 Hz, 1H), 8.05 (d, J=8.0 Hz, 1H); $^{13}$C NMR (100 MHz, DMSO-d$_6$) δ 10.5, 27.1, 33.5, 44.7, 121.4, 125.2, 126.4, 126.5, 128.5, 128.7, 130.3, 134.1, 138.1, 143.1, 158.7, 160.5; Anal. (C$_{18}$H$_{17}$ClN$_2$O) C, H, N. Calcd: 69.12, 5.48, 8.96. Found: 69.11, 5.38, 8.94.

Step 2: Preparation of ethyl 4-((2-ethyl-3,4-dihydro-4-oxo-3-phenethylquinazolin-8-yl)methyl)benzoate

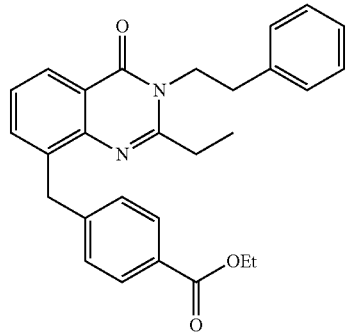 [SMILES: CCOC(=O)c1ccc(Cc2cccc3c(=O)n(CCc4ccccc4)c(CC)nc23)cc1]

The solid (2.8 g, 8.95 mmol) from step 1 mixed with Pd$_2$(dba)$_3$ (0.169 g, 0.18 mmol) and [(t-Bu)PH]BF$_4$ (0.207 g, 0.71 mmol) in NMP (20 mL) was added at rt with mixture of Zn (0.64 g, 9.79 mmol) and ethyl 4-(bromomethyl)benzoate (2.28 g, 9.47 mmol) prestirred at rt for 5 h. Then the reaction mixture was irradiated With microwave 250 W at 175° C. for 25 min. The resulting mixture was applied to column chromatography eluting with EA/Hexane (1:4) to give title compound as white solid (1.84 g, 44.1%).

Steps 3-5: Preparation of 4-((2-ethyl-3,4-dihydro-4-oxo-3-phenethylquinazolin-8-yl)methyl)-N-hydroxybenzamide (Compound 4c)

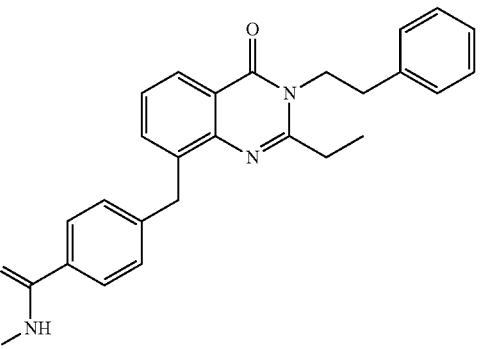

4c

The white solid (1.3 g, 2.95 mmol) of step 2, dissolved in mixture of THF (20 mL) and MeOH (4 mL) was added with aqueous LiOH solution (2.5 M) and stirred at rt for 24 h. The resulting solution was evaporated to dry, suspended in water (100 mL), and acidified with 1 N HCl to pH3 to get precipitate formed. The solution was filtered to give white solid. Then the solid mixed with NH$_2$OBn.HCl (0.52 g, 3.26 mmol), EDCl (0.62 g, 3.24 mmol), HOBt (0.45 g, 3.26 mmol), and triethyl amine (0.45 mL, 3.25 mmol) in CH$_2$Cl$_2$ (30 mL) was stirred at rt for 15 h. After 15 h, the reaction mixture was evaporated to dry and suspended in EA (50 mL). The EA solution was washed with water (3×50 mL), and the EA layer dried over MgSO$_4$ was evaporated to get beige solid. The beige solid was mixed with palladium on charcoal (10%, 0.13 g) in mixture of MeOH (21 mL) and THF (7 mL) under Ar. The reaction vessel was evacuated and followed by charging with H$_2$ to 1 atm. This cycle was repeated three times. Then the reaction mixture was stirred for 3 h at rt under $H_2$. After 3 h, the resulting mixture was filtered by celite, and the filtrate was purified by column chromatography to give compound 4c as white solid (0.62 g, three steps 49.1%); $R_f$=0.37 (MeOH/CHCl$_3$=1:9); mp=204-206° C. (dec) (recrystallized from methanol/acetonitrile) $^1$H NMR (400 MHz, DMSO-d$_6$) δ 1.24 (t, J=7.2 Hz, 3H), 2.8.1 (q, J=7.2 Hz, 2H), 2.94 (dd, J=8.0 Hz, 2H), 4.20 (dd, J=8.0 Hz, 2H), 4.38 (s, 2H), 7.25-7.43 (m, 8H), 7.61-7.63 (m, 2H), 7.72 (dd, J=7.2 and 1.2 Hz, 1H), 8.01 (dd, J=8.0 and 1.2 Hz, 1H), 8.94 (br s, 1H), 11.08 (br s, 1H); $^{13}$C NMR (100 MHz, DMSO-d$_6$) δ 10.5, 26.9, 33.6, 35.6, 44.5, 120.1, 124.5, 126.0, 126.5, 126.8, 128.5, 128.6, 128.7, 130.3, 134.5, 137.6, 138.2, 144.6, 144.7, 156.8, 161.2, 164.1; ESIMS(−) m/z 426.0 [M−1]$^-$. Anal. ($C_{26}H_{25}N_3O_3$) C, H, N. Calcd: 73.05, 5.89, 9.83. Found: 72.79, 5.81, 9.81.

EXAMPLE 5

Preparation of 4-(2-ethyl-3,4-dihydro-4-oxo-3-phenethylquinazolin-8-yl)-N-hydroxybenzamide (Compound 5a)

Step 1: Preparation of 8-chloro-2-ethyl-3-phenethylquinazolin-4(3H)-one

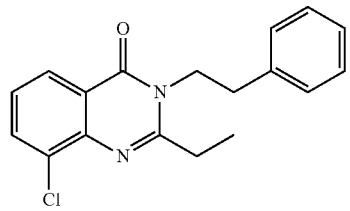 [SMILES: CCc1nc2c(Cl)cccc2c(=O)n1CCc1ccccc1]

The title compound was prepared using the procedure described above of the step 1 of example 1 from 3-chloroanthranilic acid (5 g, 29.14 mmol) to give white needle crystal (4.3 g, 47.2%); $R_f$=0.53 (EA/Hexane=1:2); $^1$H NMR (400 MHz, DMSO-d$_6$) δ 1.24 (t, J=7.2 Hz, 3H), 2.79 (q, J=7.2 Hz, 2H), 2.94 (t, J=7.6 Hz, 2H), 4.20 (t, J=7.6 Hz, 2H), 7.20-7.31 (m, 5H), 7.41 (dd, J=8.0, 7.6 Hz, 1H), 7.89 (d, J=7.6 Hz, 1H), 8.05 (d, J=8.0 Hz, 1H); $^{13}$C NMR (100 MHz, DMSO-d$_6$) δ 10.5, 27.1, 33.5, 44.7, 121.4, 125.2, 126.4, 126.5, 128.5, 128.7, 130.3, 134.1, 138.1, 143.1, 158.7, 160.5; Anal. ($C_{18}H_{17}ClN_2O$) C, H, N. Calcd: 69.12, 5.48, 8.96. Found: 69.11, 5.38, 8.94.

Step 2: Preparation of methyl 4-(2-ethyl-3,4-dihydro-4-oxo-3-phenethylquinazolin-8-yl)benzoate

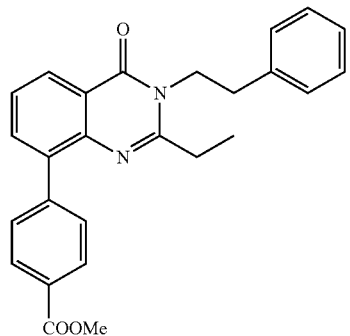 [SMILES: CCc1nc2c(-c3ccc(C(=O)OC)cc3)cccc2c(=O)n1CCc1ccccc1]

The white crystal (3.7 g, 11.83 mmol) from step 1 mixed with Herrmann's palladacycle (0.166 g, 0.18 mmol), [(t-Bu)PH]BF$_4$(0.206 g, 0.71 mmol), cesium carbonate (3.87 g, 11.82 mmol), and DBU (0.18 mL, 1.20 mmol) in DMF (30 mL) under Ar was added with 4-(carbomethoxy)phenylboronic acid (2.17 g, 11.82 mmol). The reaction mixture was irradiated with microwave 120 W to reflux for 20 min. After irradiation, the resulting mixture was evaporated to get oil residue. The residue suspended in EA (50 mL) was washed with water (3×50 mL). The EA layer dried over MgSO4 was evaporated to give title compound as beige solid (2.57 g, 52.7%). $R_f$=0.11 (EA/Hexane=1:4); $^1$H NMR (400 MHz, CDCl$_3$) δ 1.14 (t, J=7.2 Hz, 3H), 2.62 (q, J=7.2 Hz, 2H), 2.97 (dd, J=7.6 Hz, 2H), 4.23 (dd, J=7.6 Hz, 2H), 7.18-7.27 (m, 5H), 7.45 (t, J=7.6 Hz, 1H), 7.69-7.71 (m, 2H), 7.74 (dd, J=7.6 and 1.2 Hz, 1H), 8.03-8.05 (m, 2H), 8.28 (dd, J=8.0 and 1.6 Hz, 1H); $^{13}$C NMR (100 MHz, CDCl$_3$) δ 10.7, 28.0, 34.7, 45.3, 52.1, 121.2, 126.2, 126.9 (2C), 127.2, 128.7, 128.83, 128.85, 128.9, 130.2, 130.7, 134.8, 137.5, 138.0, 143.2, 144.3, 156.4, 162.3, 167.2;

Steps 3-5: Preparation of 4-(2-ethyl-3,4-dihydro-4-oxo-3-phenethylquinazolin-8-yl)-N-hydroxybenzamide (Compound 5a)

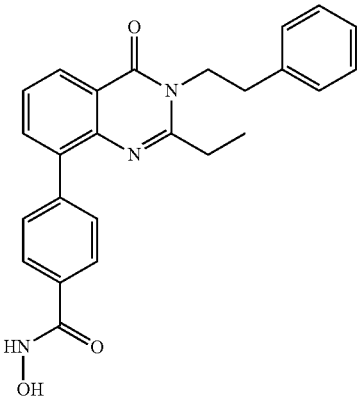

5a

The title compound 5a was prepared using the procedure described above of the step 3, step 4, and step 5 of example 4 from the beige solid (2 g, 4.85 mmol) of step 2 of example 5 to give compound 5a (1199 g, three steps 49.4%) as white solid. $R_f$=0.36 (MeOH/CHCl$_3$=1:9); mp=202-204° C. (dec) (recrystallized from dichloromethane); $^1$H NMR (400 MHz, DMSO-d$_6$) δ 1.10 (t, J=7.2 Hz, 3H), 2.76 (q J=7.2 Hz, 2H), 2.96 (dd, J=7.6 Hz, 2H), 4.23 (dd J=7.6 Hz, 2H), 7.21-7.33 (m, 5H), 7.57 (dd, J=7.61 Hz, 1H), 7.75-7.83 (m, 4H), 7.87 (br d, J=6.4 Hz, 1H), 8.18 (br d, J=6.8 Hz, 1H), 9.04 (br s, 1H), 11.27 (br s, 1H), $^{13}$C NMR (100 MHz, DMSO-d$_6$) δ 10.4, 27.0, 33.6, 44.5, 120.6, 126.1, 126.2, 126.5, 128.5, 128.7, 130.3, 131.3, 134.7, 136.7, 138.2, 140.7, 143.7, 157.1, 161.1, 164.0; ESIMS(−) m/z 412.0 [M−1]$^-$. Anal. ($C_{25}H_{23}N_3O_3$.1/10H$_2$O) C, H, N. Calcd: 72.31, 5.63, 10.12. Found: 72.10, 5.58, 9.93.

EXAMPLE 6

Preparation of (2E)-N-(2-aminophenyl)-3-(3,4-dihydro-2-methyl-4-oxo-3-phenethylquinazolin-7-yl)acrylamide (Compound 6a)

Step 1: Preparation of 7-chloro-2-methyl-3-phenethylquinazolin-4(3H)-one

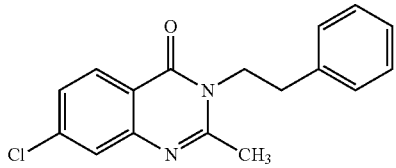 [SMILES: Cc1nc2cc(Cl)ccc2c(=O)n1CCc1ccccc1]

4-chloroanthranilic acid (6 g, 34.27 mmol) suspended in acetic anhydride (25 mL, 264.47 mmol) was refluxed for 3 h. The resulting solution was cooled to rt to give crystal formed. The solution was filtered and washed with excess of hexane to get light yellow needle crystal. The crystal was mixed with phenethylamine (4.6 mL, 36.15 mmol) in acetic acid (25 mL) and refluxed for 18.5 h. After 18.5 h, the reaction mixture was diluted with dichloromethane (50 mL) and washed with water (3×50 mL) and saturated aqueous NaHCO$_3$ solution (7×40 mL). The organic layer dried over MgSO$_4$ was concentrated to around 20 mL and added with excess of MeOH to get crystal formed. The solution was filtered to give title compound as white crystal (5.2 g, 50.8%). R$_f$=0.3 (ethyl acetate/hexane=1:2); mp 133-135° C. (recrystallized from methanol); $^1$H NMR (400 MHz, DMSO-d$_6$) δ 2.46 (s, 3H, CH$_3$), 2.96 (t, J=8 Hz, 2H, CH$_2$), 4.20 (t, J=8 Hz, 2H, CH$_2$), 7.23-7.25 (m, 3H, ArH), 7.28-7.32 (m, 2H, ArH), 7.49 (dd, 1H, J=8.4, 2 Hz, 7.60 (d, J=2 Hz, 1H, ArH), 8.09 (d, J=8.4 Hz, 1H, ArH); $^{13}$C NMR (50 MHz, DMSO-d$_6$) δ 23.2, 33.9, 46.2, 119.2, 126.1, 127.0, 127.1, 128.7, 129.1, 129.3, 138.7, 139.4, 148.6, 157.1, 160.9; ESIMS(+) m/z 299.0 [M+1]$^+$. Anal. (C$_{17}$H$_{15}$ClN$_2$O) C, H, N. Calcd: 68.34, 5.06, 9.38. Found: 68.56, 5.07, 9.57.

Step 2: Preparing (2E)-ethyl 3-(3,4-dihydro-2-methyl-4-oxo-3-phenethylquinazolin-7-yl)acrylate

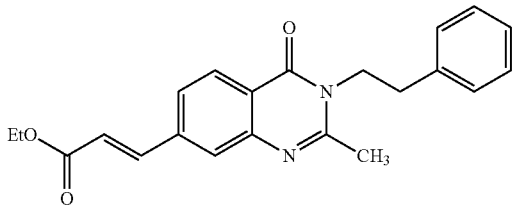 [SMILES: CCOC(=O)/C=C/c1ccc2c(=O)n(CCc3ccccc3)c(C)nc2c1]

The title compound was prepared using the similar procedure described above of the step 2 of example 1 from the beige solid (4.5 g, 15.06 mmol) of title compound of step 1 of example 6 to give light yellow solid (3.5 g, 64.1%). R$_f$=0.2 (ethylacetate/hexane=1:2), mp 149-151° C. (recrystallized from ethylacetate); $^1$H NMR (400 MHz, DMSO-d$_6$) δ 1.26 (t, J=7.2 Hz, 3H, CH$_3$), 2.47 (s, 3H, CH$_3$), 2.96 (t, J=8 Hz, 2H, CH$_2$), 4.18-4.23 (m, 4H, CH$_2$), 6.81 (d, J=16 Hz, 1H, C=CH), 7.23-7.33 (m, 5H, ArH), 7.76 (d, J=16 Hz, 1H, C=CH), 7.82-7.86 (m, 2H, ArH), 8.09 (d, J=8 Hz, 1H, ArH); $^{13}$C NMR (100 MHz, DMSO-d$_6$) δ 14.1, 22.6, 33.4, 45.6, 60.2, 120.7, 121.1, 124.8, 126.5, 126.6, 127.0, 128.5, 128.7, 138.2, 139.5, 143.0, 147.3, 155.6, 160.6, 165.8; ESIMS(+) m/z 363.1 [M+1]$^+$. Anal. (C$_{22}$H$_{22}$N$_2$O$_3$) C, H, N. Calcd: 72.91, 6.12, 7.73. Found: 72.73, 6.09, 7.86.

Steps 3-4: Preparing (2E)-N-(2-aminophenyl)-3-(3,4-dihydro-2-methyl-4-oxo-3-phenethylquinazolin-7-yl)acrylamide (Compound 6a)

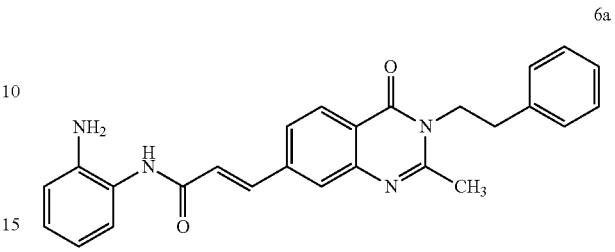

The solid (1 g, 2.76 mmol) from step 2 was mixed with aqueous LiOH (2.5 M) in mixture of THF (20 mL) and MeOH (4 mL) and stirred at rt for 1.5 h. The resulting solution was poured to ice water (50 mL) and acidified with 3 N HCl (3 mL) to pH1. Then the solution was filtered to get crude white solid. Then the solid dissolved in THF (20 mL) was added with EDCl (0.66 g, 3.37 mmol) and stirred at rt for 45 min. Then 1,2-diaminobenzene, (2.11 g, 19.12 mmol) was added to the reaction mixture and kept stirring at rt for 24 h. After 24 h, the resulting mixture was evaporated to dry and suspended in EA (70 mL) and washed with water (3×50 mL and saturated aqueous NaHCO$_3$ (4×30 mL). The organic layer dried over MgSO$_4$ was evaporated to get yellow solid. The yellow solid was suspended in MeOH (50 mL) and filtered to give compound 6a as yellow solid (0.707 g, two steps 69.7%). mp 246-248° C. (dec) (amorphous yellow solid); $^1$H NMR (400 MHz, DMSO-d$_6$) δ2.48 (s, 3H, CH$_3$), 2.97 (t, J=8 Hz, 2H, CH$_2$), 4.22 (t, J=8 Hz, 2H, CH$_2$), 4.97 (br s, 2H, NH$_2$), 6.58 (t, J=7.6 Hz, 1H, ArH), 6.76 (d, J=8 Hz, 1H, ArH), 6.92 (t, J=7.6 Hz, 1H, ArH), 7.09 (d, J=16 Hz, 1H, C=CH), 7.22-7.37 (m, 6H, ArH), 7.65-7.76 (m, 3H, ArH, C=CH), 8.15 (d, J=8.4 Hz, 1H, ArH), 9.46 (br s, 1H, NH); $^{13}$C NMR (100 MHz, DMSO-d$_6$) δ 22.7, 33.5, 45.6, 115.9, 116.2, 120.2, 123.2, 124.2, 124.7, 125.4, 125.9, 126.2, 126.5, 126.8, 128.5, 128.7, 138.2, 140.5, 141.6, 147.4, 155.6, 160.6, 163.0; ESIMS(+) m/z 425.1 [M+1]$^+$; Anal. (C$_{26}$H$_{24}$N$_4$O$_2$.0.4H$_2$O) C, H, N. Calcd: 72.34, 5.79, 12.98. Found: 72.18, 5.76, 13.34.

Compounds Prepared Using Similar Procedures Described in Scheme 1 and Example 1

(2E)-3-(3,4-dihydro-2-methyl-4-oxo-3-phenylquinazolin-5-yl)-N-hydroxyacrylamide (1a)

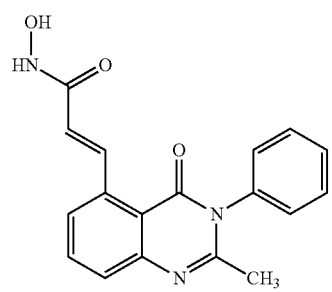 [SMILES: Cc1nc2cccc(/C=C/C(=O)NO)c2c(=O)n1-c1ccccc1]

R$_f$=0.2 (MeOH/CHCl$_3$=1:9); mp 233-235° C. (dec); $^1$H NMR (400 MHz, DMSO-d$_6$) δ 2.28 (s, 3H), 6.34 (d, J=15.6

Hz, 1H), 7.47-7.69 (n, 6H), 7.88-7.95 (m, 2H), 8.54 (d, J=16 Hz), $^{13}$C NMR (100 MHz, DMSO-d$_6$) δ 22.2, 117.0, 122.8, 123.9, 126.5, 128.2, 129.6, 129.8, 135.1, 136.4, 137.6, 137.8, 143.9, 157.9, 160.3, 162.2; ESIMS(+) m/z 322.1 [M+Na]$^+$.

(2E)-3-(3,4-dihydro-2-methyl-4-oxo-3-phenylquinazolin-7-yl)-N-hydroxyacrylamide (1c)

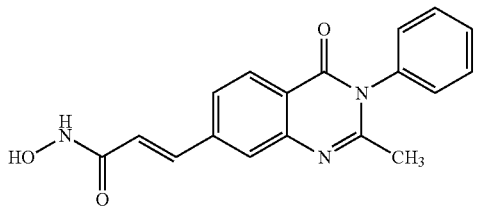 [SMILES: Cc1nc2cc(/C=C/C(=O)NO)ccc2c(=O)n1-c1ccccc1]

R$_f$=0.45 (methanol/chloroform=1:5), mp 239-240° C. (dec) (recrystallized from methanol/acetonitrile); $^1$H NMR (400 MHz, DMSO-d$_6$) δ 2.11 (s, 3H), 6.67 (d, J=16.0 Hz, 1H), 7.42-7.68 (m, 7H), 7.78 (br s, 1H), 8.07 (d, J=8.0 Hz, 1H), 9.18 (br s, 1H), 10.90 (br s, 1H); $^{13}$C NMR (100 MHz, DMSO-d$_6$) δ 24.0, 120.6, 122.3, 124.3, 126.1, 126.9, 128.4, 128.9, 129.5, 137.1, 137.7, 140.7, 147.7, 155.1, 160.9, 162.1; ESIMS(-) m/z 320.01 [M-1]$^-$. Anal. (C$_{18}$H$_{15}$N$_3$O$_3$) C, H, N. Calcd: 67.28, 4.71, 13.08. Found: 67.29, 4.87, 13.45.

(2E)-3-(3,4-dihydro-2-methyl-4-oxo-3-phenylquinazolin-8-yl)-N-hydroxyacrylamide (1d)

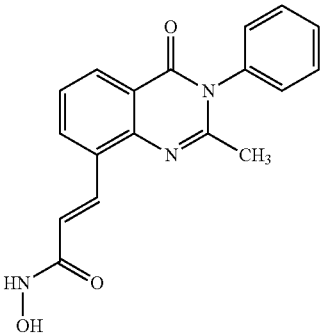 [SMILES: Cc1nc2c(/C=C/C(=O)NO)cccc2c(=O)n1-c1ccccc1]

R$_f$=0.23 (MeOH/CHCl$_3$=1:9); mp=169-171° C. (dec), $^1$H NMR (400 MHz, DMSO-d$_6$) δ 2.18 (s, 3H), 6.80 (d, J=16 Hz, 1H), 7.45-7.47 (m, 2H), 7.50-7.59 (m, 4H), 8.06-8.11 (m, 2H), 8.32 (d, J=16 Hz, 1H), 9.08 (br s, 1H), 10.86 (br s, 1H); $^{13}$C NMR (100 MHz, DMSO-d$_6$) δ 24.3, 121.1, 121.2, 126.2, 127.4, 128.3, 129.0, 129.5, 130.9, 131.7, 133.5, 137.7, 145.1, 154.4, 161.1, 162.8, ESIMS(-) m/z 320.0 [M-1]$^-$. Anal. (C$_{18}$H$_{15}$N$_3$O$_3$.1/3CHCl$_3$) C, H, N. Calcd: 60.98, 4.28, 11.64. Found: 61.23, 4.42, 11.65.

(2E)-3-(3-benzyl-3,4-dihydro-2-methyl-4-oxo-quinazolin-7-yl)-N-hydroxyacrylamide (1e)

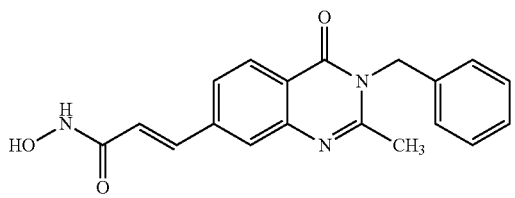 [SMILES: Cc1nc2cc(/C=C/C(=O)NO)ccc2c(=O)n1Cc1ccccc1]

R$_f$=0.45 (MeOH/CHCl$_3$=1:7); mp 216-218° C. (dec) (recrystallized from methanol/acetonitrile); $^1$H NMR (400 MHz, DMSO-d$_6$) δ 2.48 (s, 3H), 5.36 (s, 2H), 6.66 (d, J=15.6 Hz, 1H), 7.18 (br d, J=7.6 Hz, 2H), 7.25-7.35 (m, 3H), 7.59 (d, J=16 Hz, 1H), 7.68 (d, J=8.8 Hz, 1H), 7.75 (br s, 1H), 8.14 (d, J=8 Hz, 1H), 9.15 (br s, 1H), 10.87 (br s, 1H); $^{13}$C NMR (100 MHz, DMSO-d$_6$) δ22.9, 46.3, 120.0, 122.3, 124.4, 126.1, 126.3, 127.1, 127.3, 128.8, 136.4, 137.1, 140.7, 147.5, 155.9, 161.1, 162.2; ESIMS(-) 334.0 [M-1]$^-$. Anal. (C$_{19}$H$_{17}$N$_3$O$_3$) C, H, N. Calcd: 68.05, 5.11, 12.53. Found: 67.88, 5.06, 12.20.

(2E)-3-(3,4-dihydro-2-methyl-4-oxo-3-phenethylquinazolin-7-yl)-N-hydroxyacrylamide (1f)

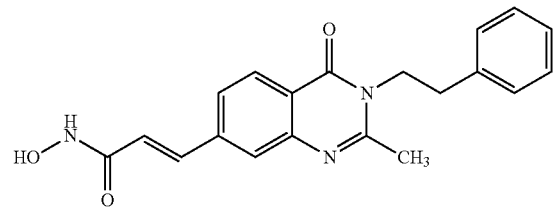 [SMILES: Cc1nc2cc(/C=C/C(=O)NO)ccc2c(=O)n1CCc1ccccc1]

R$_f$=0.25 (methanol/chloroform 1:9); mp 227-229° C. (dec) (recrystallized from methanol/acetonitrile); $^1$H NMR (400 MHz, DMSO-d$_6$) δ2.45 (s, 3H), 2.96 (t, J=7.6 Hz, 2H), 4.21 (t, J=7.6 Hz, 2H), 6.66 (d, J=16 Hz, 1H), 7.21-7.32 (m, 5H), 7.57 (d, J=16 Hz, 1H), 7.65 (d, J=8.4 Hz, 1H), 7.70 (br s, 1H), 8.11 (d, J=8.4 Hz, 1H), 9.15 (br s, 1H), 10.90 (br s, 1H); $^{13}$C NMR (100 MHz, DMSO-d$_6$) δ22.6, 33.5, 45.6, 120.1, 122.2, 124.1, 125.9, 126.5, 126.7, 128.5, 128.7, 137.0, 138.2, 140.4, 147.4, 155.6, 160.6, 162.1; ESIMS(-) m/z: 348.0 [M-1]$^-$. Anal. (C$_{20}$H$_{19}$N$_3$O$_3$) C, H, N, Calcd: 68.75, 5.48, 12.03. Found: 68.81, 5.51, 12.17.

(2E)-3-(3-(2-(1H-indol-3-yl)ethyl)-3,4-dihydro-2-methyl-4-oxoquinazolin-7-yl)-N-hydroxyacrylamide (1g)

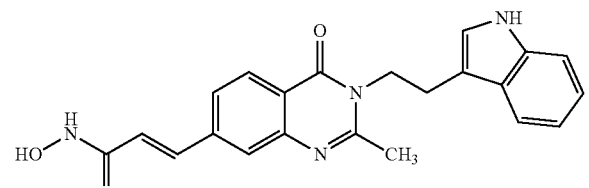

R$_f$=0.38 (MeOH/CHCl$_3$=1:7); $^1$H NMR (400 MHz, DMSO-d$_6$) δ 2.47 (s, 3H), 3.09 (t, J=7.6 Hz, 2H), 4.26 (t, J=7.6 Hz, 2H), 6.65 (d, J=15.6 Hz, 1H), 6.97 (dd, J=7.6, 7.2 Hz, 1H), 7.07 (dd, J=7.6, 7.2 Hz, 1H), 7.17 (d, J=2 Hz, 1H), 7.35 (d, J=8.0 Hz, 1H), 7.56-7.70 (m, 4H), 8.15 (d, J=8.4 Hz, 1H), 9.16 (br s, 1H), 10.88 (br s, 2H); $^{13}$C NMR (100 MHz, DMSO-d$_6$) δ22.7, 23.6, 45.1, 110.5, 111.4, 118.1, 118.4, 120.2, 121.1, 122.1, 123.2, 124.1, 125.9, 126.8, 127.0, 136.2, 137.1, 140.4, 147.5, 155.6, 160.7, 162.1; ESIMS(-) m/z 387.0 [M-1]$^-$. Anal. (C$_{22}$H$_{20}$N$_4$O$_3$.1.2H$_2$O) C, H, N, Calcd: 64.44, 5.51, 13.66. Found: 64.77, 5.51, 13.30.

(2E)-3-(3,4-dihydro-4-oxo-3-phenethylquinazolin-7-yl)-N-hydroxyacrylamide (1h)

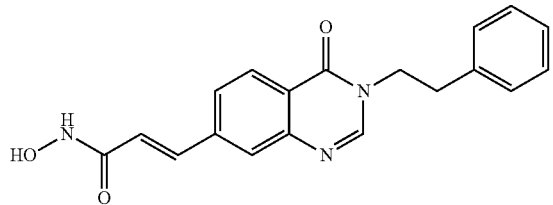 [SMILES: O=C(/C=C/c1ccc2c(=O)n(CCc3ccccc3)cnc2c1)NO]

$R_f$=0.33 (methanol/dichloromethane=1:19); mp 197-199° C. (dec) (recrystallized from methanol/acetonitrile); $^1$H NMR (400 MHz, DMSO-$d_6$) δ 3.00 (t, J=7.2 Hz, 2H), 4.19 (t, J=7.2 Hz, 2H), 6.69 (d, J=16 Hz, 1H), 7.18-7.29 (m, 5H), 7.57 (d, J=15.6 Hz, 1H), 7.70 (d, J=8.4 Hz, 1H), 7.76 (br s, 1H), 8.13-8.18 (m, 2H), 9.16 (br s, 1H), 10.95 (br s, 1H); $^{13}$C NMR (100 MHz, DMSO-$d_6$) δ 34.2, 47.4, 121.6, 122.5, 125.1, 126.4, 126.6, 126.7, 128.5, 128.8, 136.9, 137.8, 140.5, 148.3, 148.5, 159.8, 162.1; ESIMS(−) m/z 334.0 [M−1]$^-$. Anal. ($C_{19}H_{17}N_3O_3 \cdot 1H_2O$) C, H, N. Calcd: 64.58, 5.42, 11.89. Found: 64.57, 5.47, 11.55.

(2E)-3-(2-ethyl-3,4-dihydro-4-oxo-3-phenethylquinazolin-7-yl)-N-hydroxyacrylamide (1i)

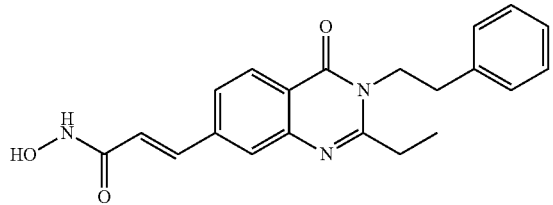 [SMILES: CCc1nc2cc(/C=C/C(=O)NO)ccc2c(=O)n1CCc1ccccc1]

$R_f$=0.25 methanol/dichloromethane=1:9); mp 209-211° C. (recrystallized from methanol; acetonitrile); $^1$H NMR (400 MHz, DMSO-$d_6$) δ 1.21 (t, J=7.2 Hz, 3H), 2.76 (q, J=7.2 Hz, 2H), 2.94 (t, J=7.6 Hz, 2H), 4.20 (t, J=7.6 Hz, 2H), 6.68 (d, J=16.0 Hz, 1H), 7.20-7.31 (m, 5H), 7.56 (d, J=16.0 Hz, 1H), 7.64 (br d, J=8.4 Hz, 1H), 7.71 (br s, 1H), 8.10 (d, J=8.0 Hz, 1H), 9.25 (br s, 1H), 10.84 (br s, 1H); $^{13}$C NMR (100 MHz, DMSO-$d_6$) δ 10.7, 27.0, 33.6, 44.6, 120.0, 122.2, 124.3, 126.0, 126.5, 126.8, 128.5, 128.7, 136.9, 138.2, 140.5, 147.2, 158.5, 160.7, 162.1; ESIMS(−) m/z 362.1 [M−1]$^-$. Anal. ($C_{21}H_{21}N_3O_3$) C, H, N. Calcd: 69.41, 5.82, 11.56. Found: 69.35, 5.79, 11.50.

(2E)-3-(2-ethyl-3,4-dihydro-4-oxo-3-(3-phenylpropyl)quinazolin-7-yl)-N-hydroxyacrylamide (1j)

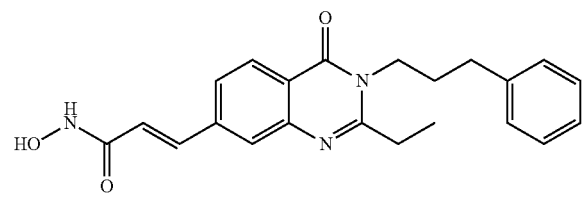 [SMILES: CCc1nc2cc(/C=C/C(=O)NO)ccc2c(=O)n1CCCc1ccccc1]

$R_f$=0.25 (methanol/chloroform=1:9); mp=189-191° C.; $^1$H NMR (400 MHz, DMSO-$d_6$) δ 1.22 (t, J=7.2 Hz, 3H), 1.92 (p, J=7.6 Hz, 2H), 2.68 (dd, J=7.6 Hz, 2H), 2.77 (q, J=7.2 Hz, 2H), 4.00 (dd, J=7.6 Hz, 2H), 6.68 (d, J=15.6 Hz, 1H), 7.14-7.18 (m, 1H), 7.23-7.29 (m, 4H), 7.54 (d, J=15.6 Hz, 1H), 7.62 (br d, J=8.0 Hz, 1H) 7.69 (br s, 1H), 8.06 (d, J=8.4 Hz, 1H); $^{13}$C NMR (100 MHz, DMSO-$d_6$) δ 10.9, 27.0, 29.4, 32.4, 42.7, 120.0, 122.3, 124.2, 125.9 (2C), 126.7, 128.2, 128.3, 136.8, 140.4, 140.9, 147.2, 158.5, 160.7, 162.0; ESIMS(−) m/z 376.0 [M−1]$^{31}$. Anal. ($C_{22}H_{23}N_3O_3$) C, H, N. Calcd: 70.01, 6.14, 11.13. Found: 69.74, 6.08, 11.11.

(2E)-3-(2-cyclopropyl-3,4-dihydro-4-oxo-3-phenethylquinazolin-7-yl)-N-hydroxyacrylamide (1k)

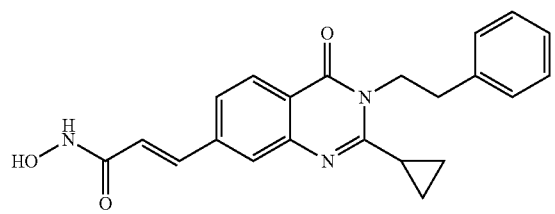 [SMILES: O=C(/C=C/c1ccc2c(=O)n(CCc3ccccc3)c(C3CC3)nc2c1)NO]

$R_f$=0.27 (MeOH/CHCl$_3$=1:9); mp=204-206° C. (dec) (recrystallized from methanol/acetonitrile); $^1$H NMR (400 MHz, DMSO-$d_6$) δ 1.01-1.10 (m 4H), 2.20-2.26 (m, 1H), 3.00 (dd, J=8.0 Hz, 2H), 4.43 (dd, J=8.0 Hz, 2H), 6.64 (d, J=15.6 Hz, 1H), 7.20-7.3.1 (m, 5H), 7.54 (d, J=16 Hz, 1H), 7.59-7.61 (m, 2H), 8.06 (d, J=8.4 Hz, 1H), 9.17 (br s, 1H), 10.85 (br s, 1H); $^{13}$C NMR (100 MHz, DMSO-$d_6$) δ 9.0 (2C), 13.6, 34.0, 44.5, 119.9, 122.2, 124.0, 125.8, 126.5, 126.8, 128.5, 128.8, 137.1, 138.1, 140.4, 147.4, 158.6, 160.7, 162.2, ESIMS(−) m/z 373.9 [M−1]$^-$. Anal. ($C_{22}H_{21}N_3O_3$) C, H, N. Calcd: 70.38, 5.64, 11.19. Found: 70.41, 5.59, 11.23.

(2E)-3-(3,4-dihydro-2-isopropyl-4-oxo-3-phenethylquinazolin-7-yl)-N-hydroxyacrylamide (1l)

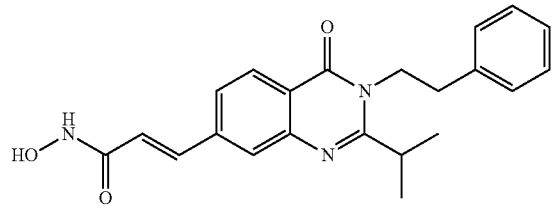 [SMILES: CC(C)c1nc2cc(/C=C/C(=O)NO)ccc2c(=O)n1CCc1ccccc1]

$R_f$=0.27 (MeOH/CHCl$_3$=1:9); mp 173-174° C. (dec) (recrystallized from methanol/acetonitrile); $^1$H NMR (400 MHz, DMSO-$d_6$) δ 1.13 (d, J=6.4 Hz, 6H), 2.93-3.00 (m, 3H, CH$_2$ and CH), 4.27 (dd, J=7.4 Hz, 2H), 6.67 (d, J=16 Hz, 1H), 7.18-7.29 (m, 5H), 7.57 (d, J=16 Hz, 1H), 7.65 (br d, J=8.4 Hz, 7.71 (br s, 1H), 8.12 (d, J=8.0 Hz, 1H), 9.16 (br s, 1H), 10.85 (br s, 1H); $^{13}$C NMR (100 MHz, DMSO-$d_6$) δ 21.1 (2C), 31.3, 34.1, 44.2, 120.0, 122.3, 124.4, 126.0, 126.5, 126.8, 128.5, 128.8, 137.0, 138.0, 140.5, 147.2, 160.9, 162.2, 162.3; ESIMS(−) m/z 376.0 [M−1]$^-$. Anal. ($C_{22}H_{23}N_3O_3$) C, H, N. Calcd: 70.01, 6.14, 11.13. Found: 69.72, 6.14, 11.04.

(2E)-3-(3-(4-methoxyphenethyl)-2-ethyl-3,4-dihydro-4-oxoquinazolin-7-yl)-N-hydroxyacrylamide (1m)

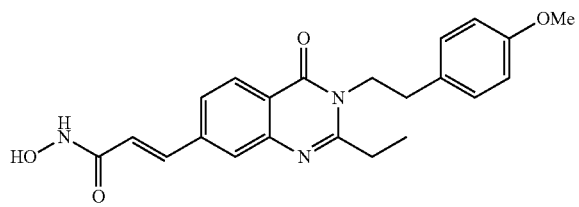 [SMILES: CCc1nc2cc(/C=C/C(=O)NO)ccc2c(=O)n1CCc1ccc(OC)cc1]

$R_f$=0.32 (MeOH/CHCl$_3$=1:9); 215-217° C.; $^1$H NMR (400 MHz, DMSO-d$_4$) δ 1.22 (t, J=7.2 Hz, 3H), 2.77 (q, J=7.2 Hz, 2H) 2.87 (dd, J=7.6 Hz, 2H), 3.70 (s, 3H), 4.16 (dd, J=7.6 Hz, 2H), 6.65 (d, J=16 Hz, 1H), 6.85-6.87 (m, 2H), 7.14-7.16 (m, 2H), 7.57 (d, J=16 Hz, 1H), 7.64 (br d, J=8.4 Hz, 1H), 7.72 (br s, 1H), 8.11 (d, J=8.0 Hz, 1H), 9.15 (br s, 1H), 10.84 (br s, 1H) $^{13}$C NMR (100 MHz, DMSO-d$_6$) δ 10.8, 27.0, 32.8, 44.8, 55.0, 113.9, 120.0, 122.2, 124.3, 126.0, 126.7, 129.7, 130.0, 137.0, 140.4, 147.2, 158.0, 158.5, 160.7, 162.1; ESIMS(-) m/z 392.0 [M-1]$^-$. Anal. (C$_{22}$H$_{23}$N$_3$O$_4$) C, H, N. Calcd: 67.16, 5.89, 10.68. Found: 66.78, 5.91, 10.33.

(2E)-3-(3-(4-fluorophenethyl)-2-ethyl-3,4-dihydro-4-oxoquinazolin-7-yl)-N-hydroxyacrylamide (1n)

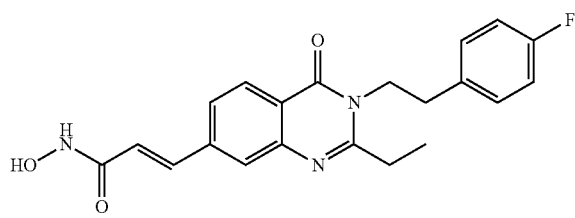 [SMILES: CCc1nc2cc(/C=C/C(=O)NO)ccc2c(=O)n1CCc1ccc(F)cc1]

$R_f$=(MeOH/CHCl$_3$=1:9): mp=mp 195-197° C. (dec); $^1$H NMR (400 MHz, DMSO-d$_6$) δ 1.23 (t, J=7.2 Hz, 3H), 2.79 (q, J=7.2 Hz, 2H), 2.94 (dd, J=7.2 Hz, 2H), 4.20 (dd, J=7.6 Hz, 2H), 6.65 (d, J=15.6 Hz, 1H), 7.10-7.15 (m, 2H), 7.27-7.30 (m, 2H), 7.57 (d, J=16 Hz, 1H), 7.65 (br d, J=8.4 Hz, 1H), 7.73 (br s, 1H) 8.11 (d, J=8.4 Hz, 1H), 9.14 (br s, 1H), 10.83 (br s, 1H); $^{13}$C NMR (100 MHz, DMSO-d$_6$) δ 10.8, 27.0, 32.8, 44.5, 115.2 (d, J=21 Hz), 120.0, 122.2, 124.3, 126.0, 126.8, 130.6 (d, J=8 Hz), 134.4 (d, J=3 Hz), 137.0, 140.5, 147.2, 158.5, 160.7, 161.0 (d, J=241 Hz), 162.1; ESIMS(-) m/z 379.9 [M-1]$^-$. Anal. (C$_{21}$H$_{20}$FN$_3$O$_3$.1/10H$_2$O) C, H, N. Calcd: 65.82, 5.31, 10.97. Found: 65.44, 5.11, 10.80.

Compounds Prepared Using Similar Procedure Described in Scheme 3 and Example 3

(2E)-3-(7-chloro-2-ethyl-3,4-dihydro-4-oxo-3-phenethylquinazolin-6-yl)-N-hydroxyacrylamide (3b)

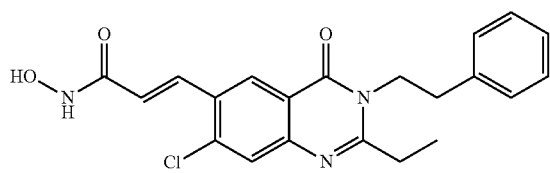 [SMILES: CCc1nc2cc(Cl)c(/C=C/C(=O)NO)cc2c(=O)n1CCc1ccccc1]

$R_f$=0.50 (MeOH/CHCl$_3$=1:9); mp=194-196° C.; $^1$H NMR (400 MHz, DMSO-d$_6$) δ 1.19 (t, J=7.2 Hz, 3H), 2.76 (q, J=7.2 Hz, 2H), 2.95 (dd, 7.6 Hz, 2H), 4.21 (dd, J=7.6 Hz, 2H), 6.64 (d, J=15.6 Hz, 1H), 7.23-7.32 (m, 5H), 7.70 (s, 1H), 7.75 (d, J=16.0 Hz, 1H), 8.34 (s, 1H), 9.21 (br s, 1H), 10.86 (br s, 1H); $^{13}$C NMR (100 MHz, DMSO-d$_6$) δ 10.6, 27.1, 33.5, 44.7, 119.1, 122.9, 124.8, 126.6, 127.3, 128.5, 128.7, 130.6, 132.4, 138.1, 138.6, 147.6, 160.1, 160.4, 161.8; ESIMS(-) m/z 395.9 [M-1]$^-$, Anal. (C$_{21}$H$_{20}$ClN$_3$O$_3$.H$_2$O) C, H, N. Calcd: 60.65, 5.33, 10.10.

Compounds Prepared Using Similar Procedure Described in Scheme 4 and Example 4

4-((2-ethyl-3,4-dihydro-4-oxo-3-phenethylquinazolin-6-yl)methyl)-N-hydroxybenzamide (4a)

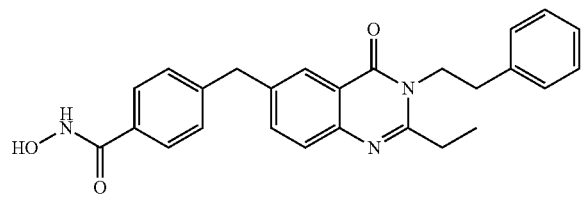 [SMILES: CCc1nc2ccc(Cc3ccc(C(=O)NO)cc3)cc2c(=O)n1CCc1ccccc1]

$R_f$=0.27 (MeOH/CHCl$_3$=1:19); mp 181-183° C. (recrystallized from methanol/acetonitrile); $^1$H NMR (400 MHz, DMSO-d$_6$) δ 1.19 (t, J=7.2 Hz, 3H), 2.74 (q, J=7.2 Hz, 2H), 2.92 (dd, J=7.6 Hz, 2H) 4.13 (s, 2H), 4.20 (dd, J=7.6 Hz, 2H), 7.22-7.35 (m, 7H), 7.54 (d, J=8.4 Hz, 1H), 7.65-7.69 (m, 3H), 7.95 (br s, 1H), 8.97 (br s, 1H), 11.13 (br s, 1H); $^{13}$C NMR (100 MHz, DMSO-d$_6$) δ 10.8, 26.8, 33.7, 40.2, 44.5, 119.7, 125.3, 126.5, 127.0, 127.1, 128.5, 128.73, 128.78, 130.7, 135.1, 138.2, 139.1, 144.1, 145.3, 157.3, 161.0, 164.1; ESIMS(-) m/z 426.0 [M-1]$^-$. Anal. (C$_{26}$H$_{25}$N$_3$O$_3$) C, H, N. Calcd; 73.05, 5.89, 9.83. Found: 72.82, 5.96, 9.84.

4-((2-ethyl-3,4-dihydro-4-oxo-3-phenethylquinazolin-7-yl)methyl)-N-hydroxybenzamide (4b)

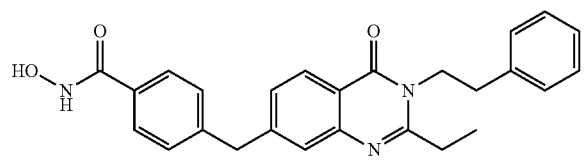 [SMILES: CCc1nc2cc(Cc3ccc(C(=O)NO)cc3)ccc2c(=O)n1CCc1ccccc1]

$R_f$=0.26 (MeOH/CHCl$_3$=1:19); mp 181-183 (dec); $^1$H NMR (400 MHz, DMSO-d$_6$) δ 1.11 (t, J=7.2 Hz, 3H), 2.63 (q, J=7.2 Hz, 2H), 2.88 (dd, J=7.6 Hz, 2H), 4.08 (s, 2H), 4.15 (dd, J=7.6 Hz, 2H), 7.15-7.26 (m, 5H), 7.31-7.38 (m, 4H), 7.62-7.64 (m, 2H), 8.00 (d, J=8.0 Hz, 1H), 9.12 (br s, 11.22 (br s, 1H); $^{13}$C NMR (100 MHz, DMSO-d$_6$) δ 11.4, 27.5, 34.1, 41.2, 45.1, 118.4, 126.6, 126.9, 127.1, 127.7, 127.9, 129.1, 129.2, 129.4, 131.0, 138.6, 144.4, 147.5, 148.3, 158.9, 161.7, 165.1; ESIMS(-) m/z 426.0 [M-1]$^-$. Anal. (C$_{26}$H$_{25}$N$_3$O$_3$, 2/5H$_2$O) C, H, N. Calcd: 71.84, 5.98, 9.67. Found: 71.97, 5.95, 9.43.

HDAC Enzymatic Assay.

These compounds had inhibitory effects on human histone deacetylases (HDAC) 1, 2, 3, 6, 8, 10 and 11 The IC$_{50}$ values were determined using the following gradings: I~IV, in which I stands for IC$_{50}$ being ≥10 μM; II stands for IC$_{50}$ being >1 μM but <10 μM; III stands for IC$_{50}$ being >0.1 μM but <1 μM, and IV stands for IC$_{50}$ being ≤0.1 μM. The HDAC enzymatic assay method is known in the art. It was found these compounds inhibited HDAC1, HDAC6 and HDAC8 with respective IC50 as follows: Compound Ia: I, IV and II, Compound Ib, 1m, 1n, 3a: II, IV and III, Compound Id, 4c: I, III and III. Compounds Ic, Ie, If, Ii, Ij, 2a, II, IV and II, Compound 1g: III, IV, and II, Compound 1h: III, IV and III, Compound 2a: II, IV, and II. Compound 3b: I, III, and II. Compound 4a: II, IV, and IV, Compound 6a: II, I, and I, respectively.

Compound 1k and 1l each showed inhibitions of HDAC1. HDAC6 with IC50 of III, and IV, respectively. The IC50 of Compound 4b against HDAC6 was IV.

Because compound 1b, 1c, 1e, 1f, 1g, 1b, 1i, 1j, 2a, 3a, 4a, 4b, and 4c showed selective inhibitions on HDAC6, the HDAC6-selective inhibitors may be used for treating autoimmunity, cancer, and many neurodegenerative diseases. (S. Minucci et al., Nat. Rev. Cancer. 2006, 6, 38-51: L. Wang et al., Nat. Rev. Drug Discov. 2009, 8, 969-81; J. P. Dompierre et al., J. Neurosci. 2007, 27, 3571-83; and A. G. Kazantsev et al., Nat. Rev. Drug Discov. 2008, 7, 854-68: all of which are incorporated herein by reference in its entireties.)

MTT or SRB assays for Cytotoxicities of HDAC inhibitors. These compounds were assayed for cytotoxicities to the following cells: A549 cells (adenocarcinomic human alveolar basal epithelial cells), HCT-116 cells (human colon carcinoma cells), PANC-1 cells (human pancreatic carcinoma, epithelial-like cell line) and HepG2 cells (human liver hepatocellular carcinoma cell line), neuronal cells PC12 (rat pheochromocytoma cell line) and SH-SY5Y (human neuroblastoma cell line). MTT (3-[4,5-dimethylthiazol-2-yl]2,5-diphenyl-tetrazolium bromide) reduction was collaborated by using trypan blue exclusion assay.

The $IC_{50}$ values were determined using the following gradings: I~V, in which I stands for $IC_{50}$ being ≥10 µM (nontoxic), II stands for $IC_{50}$ being >1 µM but <10 µM (weak toxic), III stands for $IC_{50}$ being >0.1 µM but <1 µM (toxic), and IV stands for $IC_{50}$ being ≤0.1 µM (higher toxic).

It was found that these compounds were nontoxic to neuronal and Vero cells, but cytotoxic to cancer cells (A549, HCT116, PANC1 and HepG2 solid-tumor cell lines) with respective gradings as follows: Compounds 1i and 4c: I, I, I, and II, Compounds 1m 1n, 2a: II, II, II, and II, Compound 3a: II, I, I, I, Compound 3b): II, I, III, I, Compound 4b: II, II, II, III, Compound 5a: I, I, II, I, Compound 6a: I, I, III, III, respectively.

Neurite Outgrowth Assay.

The effects of the compounds on neurite outgrowth were assayed on PC 12 and SH-SY5Y cells. It was found these compounds facilitated or promoted neurite outgrowth with EC50s (µM) as follows: Compound 1c: 15.86±12.03 and 12.68±11.54, Compound 1e: 8.21±0.37 and 8.20±0.92. Compound 1f: 6.49±0.78 and 6.77±0.96, Compound 1h: 14.51±1.47 and 4.93±1.34, Compound 1i: 7.21±0.32 and 0.88±0.45, Compound 1j: 6.95±0.82, 9.97±1.17, Compound 1k: 0.76±0.69, and >30, Compound 1l: 5.28±0.51, and 6.74±0.78, Compound 1m: 20.62±3.12, and 20.62±2.51, Compound 1n: 13.92±0.94, and 22.17±2.01. Compound 3b: 10.7±111.26, and 7.63±0.74, Compound 4a: 2.89±0.45, and 4.06±0.58. Compound 6a: 6.59±1.06, and 8.81-1.04 µM, respectively. Student's t test (p<0.005). Thus, these compounds may be used for treating neurodegenerative diseases.

Anti-Amyloid Aggregation Assay.

The effects of compounds on inhibition of β-amyloid aggregation were assayed. The levels of β-amyloid aggregates were determined by thioflavin S, BCA or CR assays (Tables 1). Thioflavin S, and Congo red are for in vitro staining of aggregated β-amyloid. Bicinchoninic acid (BCA) assay determines the total protein level or concentration.

TABLE 1

| $IC_{50}$ (µM) for zinc-mediated β-amyloid aggregation detected by three different assays | | | |
|---|---|---|---|
| Compound # | thioflavin S | BCA | CR |
| 1a | >50 | 10.1 | 30.2 |
| 1b | >50 | 10.1 | 4.8 |
| 1c | 18.4 | 11.1 | 44.1 |

TABLE 1-continued

| $IC_{50}$ (µM) for zinc-mediated β-amyloid aggregation detected by three different assays | | | |
|---|---|---|---|
| Compound # | thioflavin S | BCA | CR |
| 1d | >50 | 11.7 | 14.5 |
| 1e | 18.1 | 10.6 | 5.8 |
| 1f | 9.5 | 11.7 | 43.1 |
| 1g | 7.4 | 11.1 | 15.5 |
| 1h | 5.5 | 35.0 | 14.6 |
| 1i | 6.8 | 3.9 | 5.5 |
| 6a | 10.7 | 13.8 | 30.9 |

Accordingly, the compounds of the invention may be useful for decreasing β-amyloid aggregation toxicity, promoting neurite outgrowth, and in turn improving the function of degenerating neurons.

Neurite Synaptic Uptake Activity Analysis.

The effects of compounds on the neuronal synapse uptake of fluorescent indicator FM1-43 were assayed. The uptake of the dye indicated the synaptic function of the neurites. PC 12 and SH-SY5Y cells were used. Cells in experimental groups were treated with a test compound and FM1-43; Cells in positive control were treated with NGF and FM1-43; Cells in negative control were treated with a vehicle and FM1-43. The fluorescence in the positive control were taken as 100%.

It was found that these compounds increased the uptake of dye by PC 12 and SH-SY5Y cells with respective EC50 (µM) as follows. Compound 1a: 8.15±0.39 and 14.73±1.58, compound 1c: 15.86±2.03 and 12.68±1.54, compound 1d: 7.81±0.65 and 8.03±0.53, compound 1e: 8.21±0.37 and 8.20±0.92, compound 1f: 6.49±0.78 and 6.77±0.96, compound 1h: 14.51±1.47 and 4.932±1.34, compound 1i: 7.21±0.32 and 0.88±0.45, compound 1j: 6.95±0.82 and 9.97±1.17, compound 1k: 0.76±0.69 and >30, compound 1l: 5.28±0.51, 6.74±0.78, compound 1m: 20.62±3.12 and 20.62±2.51, compound 1n: 13.92±0.94 and 22.17±2.01, compound 3b: 10.71±1.26, 7.63±0.74, compound 4a: 2.89±0.45, 4.06±0.58, compound 6a: 6.59±1.06, 8.81±1.04 µM, respectively. Compounds 2a, 3a, 4c increased, the uptake of the dye by PC 12 with an EC50 at 1.66±0.76, 0.78±0.49, and 5.34±0.85), respectively. The data indicated that these compounds facilitated outgrowth of neurites that have functional synapse uptake activities, which is important in terms of using these compounds for treating neurodegenerative diseases and/or improving neurite functions in neurodegenerative diseases.

Rotarod test. To test the effect of the compound in improving the learning ability of the animals in Alzheimer disease model, β-aggregates-induced hippocampal lesions were used to generate learning-impaired mice. The hippocampus-lesioned mice were treated with compound 1c and 1f (daily i.p. 10 mg/kg for 30 days). FIG. 1 shows the results of rotarod test. Both compounds 1c and 1f improved learning performance as compared to the controls (vehicle) in hippocampus-lesioned mice.

A compound having the structure of Formula X:

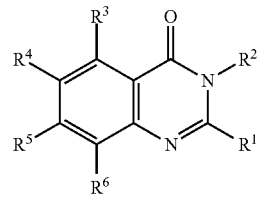

Formula X

| Cpd No. | Chemical Name | Structure | Substituents of Formula X |
|---|---|---|---|
| 1a | (2E)-3-(3,4-dihydro-2-methyl-4-oxo-3-phenylquinazolin-5-yl)-N-hydroxyacrylamide | 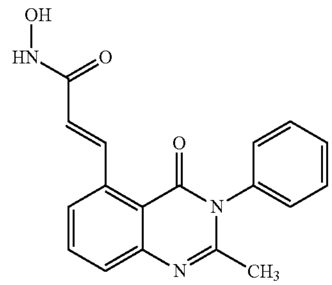 [SMILES: Cc1nc2cccc(/C=C/C(=O)NO)c2c(=O)n1-c1ccccc1] | $R^1$ = methyl<br>$R^2$ = phenyl<br>$R^3$ = (2E)-3-N hydroxyamino-3-oxo-propenyl<br>$R^4$ = hydrogen<br>$R^5$ = hydrogen<br>$R^6$ = hydrogen |
| 1b | (2E)-3-(3,4-dihydro-2-methyl-4-oxo-3-phenylquinazolin-6-yl)-N-hydroxyacrylamide | 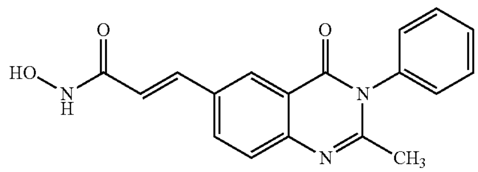 [SMILES: Cc1nc2ccc(/C=C/C(=O)NO)cc2c(=O)n1-c1ccccc1] | $R^1$ = methyl<br>$R^2$ = phenyl<br>$R^3$ = hydrogen<br>$R^4$ = (2E)-3-N-hydroxyamino-3-oxo-propenyl<br>$R^5$ = hydrogen<br>$R^6$ = hydrogen |
| 1c | (2E)-3-(3,4-dihydro-2-methyl-4-oxo-3-phenylquinazolin-7-yl)-N-hydroxyacrylamide | 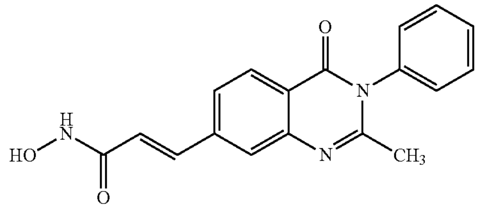 [SMILES: Cc1nc2cc(/C=C/C(=O)NO)ccc2c(=O)n1-c1ccccc1] | $R^1$ = methyl<br>$R^2$ = phenyl<br>$R^3$ = hydrogen<br>$R^4$ = hydrogen<br>$R^5$ = (2E)-3-N-hydroxyamino-3-oxo-propenyl<br>$R^6$ = hydrogen |
| 1d | (2E)-3-(3,4-dihydro-2-methyl-4-oxo-3-phenylquinazolin-8-yl)-N-hydroxyacrylamide | 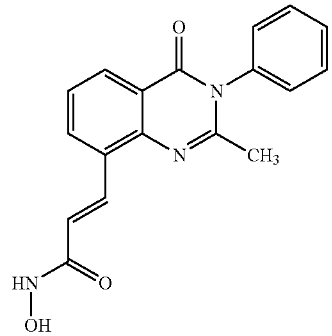 [SMILES: Cc1nc2c(/C=C/C(=O)NO)cccc2c(=O)n1-c1ccccc1] | $R^1$ = methyl<br>$R^2$ = phenyl<br>$R^3$ = hydrogen<br>$R^4$ = hydrogen<br>$R^5$ = hydrogen<br>$R^6$ = (2E)-3-N-hydroxyamino-3-oxo-propenyl |
| 1e | (2E)-3-(3-benyzl-3,4-dihydro-2-methyl-4-oxoqunazolin-7-yl)-N-hydroxyacrylamide | 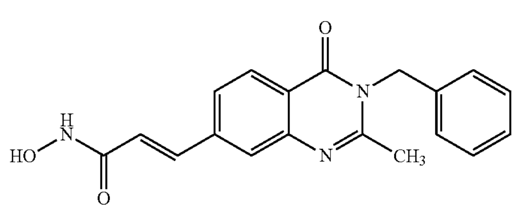 [SMILES: Cc1nc2cc(/C=C/C(=O)NO)ccc2c(=O)n1Cc1ccccc1] | $R^1$ = methyl<br>$R^2$ = benzyl<br>$R^3$ = hydrogen<br>$R^4$ = hydrogen<br>$R^5$ = (2E)-3-N-hydroxyamino-3-oxo-propenyl<br>$R^6$ = hydrogen |
| 1f | (2E)-3-(3,4-dihydro-2-methyl-4-oxo-3-phenethylquinazolin-7-yl)-N-hydroxyacrylamide | 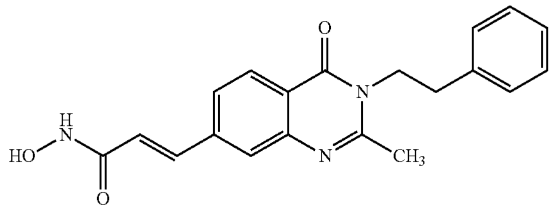 [SMILES: Cc1nc2cc(/C=C/C(=O)NO)ccc2c(=O)n1CCc1ccccc1] | $R^1$ = methyl<br>$R^2$ = 2-phenylethyl<br>$R^3$ = hydrogen<br>$R^4$ = hydrogen<br>$R^5$ = (2E)-3-N-hydroxyamino-3-oxo-propenyl<br>$R^6$ = hydrogen |

-continued

| Cpd No. | Chemical Name | Structure | Substituents of Formula X |
|---|---|---|---|
| 1g | (2E)-3-(3-(2-(1H-indol-3-yl)ethyl)-3,4-dihydro-2-methyl-4-oxoquinazolin-7-yl)-N-hydroxyacrylamide | 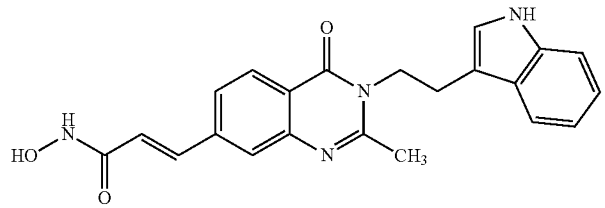 [SMILES: Cc1nc2cc(/C=C/C(=O)NO)ccc2c(=O)n1CCc1c[nH]c2ccccc12] | $R^1$ = methyl<br>$R^2$ = 2-(1H-indol-3-yl)ethyl<br>$R^3$ = hydrogen<br>$R^4$ = hydrogen<br>$R^5$ = (2E)-3-N-hydroxyamino-3-oxo-propenyl<br>$R^6$ = hydrogen |
| 1h | (2E)-3-(3,4-dihydro-4-oxo-3-phenethylquinazolin-7-yl)-N-hydroxyacrylamide | 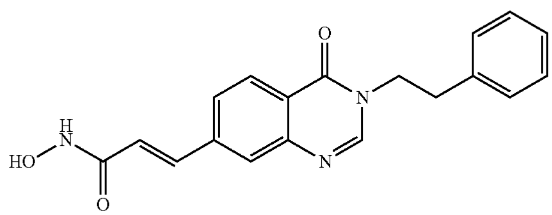 [SMILES: O=C(/C=C/c1ccc2c(=O)n(CCc3ccccc3)cnc2c1)NO] | $R^1$ = hydrogen<br>$R^2$ = 2-phenylethyl<br>$R^3$ = hydrogen<br>$R^4$ = hydrogen<br>$R^5$ = (2E)-3-N-hydroxyamino-3-oxo-propenyl<br>$R^6$ = hydrogen |
| 1i | (2E)-3-(2-ethyl-3,4-dihydro-4-oxo-3-phenethylquinazolin-7-yl)-N-hydroxyacrylamide | 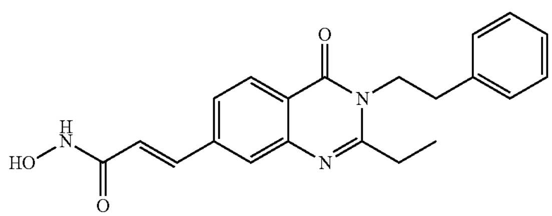 [SMILES: CCc1nc2cc(/C=C/C(=O)NO)ccc2c(=O)n1CCc1ccccc1] | $R^1$ = ethyl<br>$R^2$ = 2-phenylethyl<br>$R^3$ = hydrogen<br>$R^4$ = hydrogen<br>$R^5$ = (2E)-3-N-hydroxyamino-3-oxo-propenyl<br>$R^6$ = hydrogen |
| 1j | (2E)-3-(2-ethyl-3,4-dihydro-4-oxo-3-(3-phenylpropyl)quinazolin-7-yl)-N-hydroxyacrylamide | 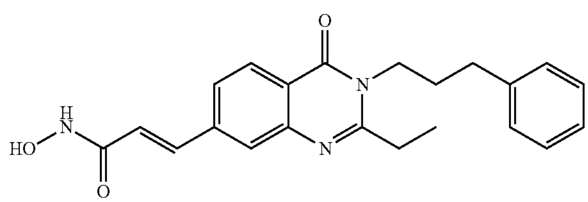 [SMILES: CCc1nc2cc(/C=C/C(=O)NO)ccc2c(=O)n1CCCc1ccccc1] | $R^1$ = ethyl<br>$R^2$ = 3-phenylpropyl<br>$R^3$ = hydrogen<br>$R^4$ = hydrogen<br>$R^5$ = (2E)-3-N-hydroxyamino-3-oxo-propenyl<br>$R^6$ = hydrogen |
| 1k | (2E)-3-(2-cyclopropyl-3,4-dihydro-4-oxo-3-phenethylquinazolin-7-yl)-N-hydroxyacrylamide | 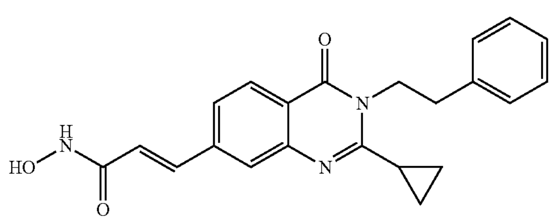 [SMILES: O=C(/C=C/c1ccc2c(=O)n(CCc3ccccc3)c(C3CC3)nc2c1)NO] | $R^1$ = cyclopropyl<br>$R^2$ = 2-phenylethyl<br>$R^3$ = hydrogen<br>$R^4$ = hydrogen<br>$R^5$ = (2E)-3-N-hydroxyamino-3-oxo-propenyl<br>$R^6$ = hydrogen |
| 1l | (2E)-3-(3,4-dihydro-2-isopropyl-4-oxo-3-phenethylquinazolin-7-yl)-N-hydroxyacrylamide | 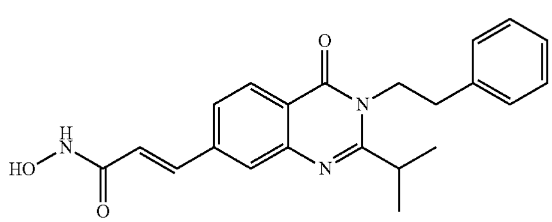 [SMILES: CC(C)c1nc2cc(/C=C/C(=O)NO)ccc2c(=O)n1CCc1ccccc1] | $R^1$ = isopropyl<br>$R^2$ = 2-phenylethyl<br>$R^3$ = hydrogen<br>$R^4$ = hydrogen<br>$R^5$ = (2E)-3-N-hydroxyamino-3-oxo-propenyl<br>$R^6$ = hydrogen |
| 1m | (2E)-3-(3-(4-methoxyphenethyl)-2-ethyl-3,4-dihydro-4-oxoquinazolin-7-yl)-N-hydroxyacrylamide | 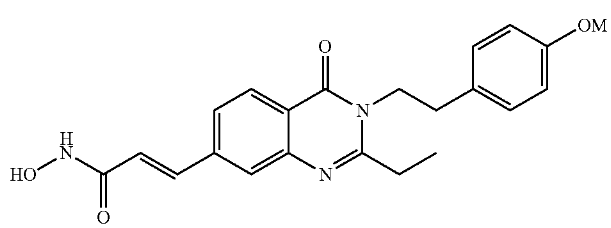 | $R^1$ = ethyl<br>$R^2$ = 2-(4-methoxyphenyl)ethyl<br>$R^3$ = hydrogen<br>$R^4$ = hydrogen<br>$R^5$ = (2E)-3-N-hydroxyamino-3-oxo-propenyl<br>$R^6$ = hydrogen |

-continued

| Cpd No. | Chemical Name | Structure | Substituents of Formula X |
|---|---|---|---|
| 1n | (2E)-3-(3-(4-fluorophenethyl-2-ethyl-3,4-dihydro-4-oxoquinazolin-7-yl)-N-hydroxyacrylamide | 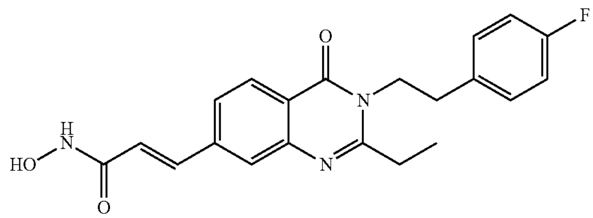 [SMILES: CCc1nc2cc(/C=C/C(=O)NO)ccc2c(=O)n1CCc1ccc(F)cc1] | $R^1$ = ethyl<br>$R^2$ = 2-(4-fluorophenyl)ethyl<br>$R^3$ = hydrogen<br>$R^4$ = hydrogen<br>$R^5$ = (2E)-3-N-hydroxyamino-3-oxo-propenyl<br>$R^6$ = hydrogen |
| 4a | 4-((2-ethyl-3,4-dihydro-4-oxo-3-phenethylquinazolin-6-yl)methyl)-N-hydroxybenzamide | 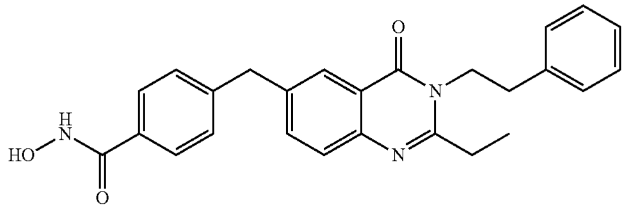 [SMILES: CCc1nc2ccc(Cc3ccc(C(=O)NO)cc3)cc2c(=O)n1CCc1ccccc1] | $R^1$ = ethyl<br>$R^2$ = 2-phenylethyl<br>$R^3$ = hydrogen<br>$R^4$ = 4-(N-hydroxyamino-carbonyl)benzyl<br>$R^5$ = hydrogen<br>$R^6$ = hydrogen |
| 4b | 4-((2-ethyl-3,4-dihydro-4-oxo-3-phenethylquinazolin-7-yl)methyl)-N-hydroxybenzamide | 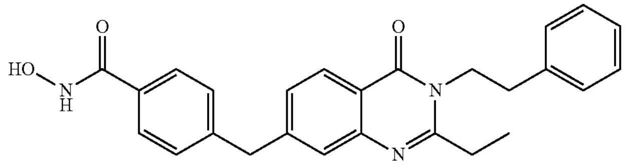 [SMILES: CCc1nc2cc(Cc3ccc(C(=O)NO)cc3)ccc2c(=O)n1CCc1ccccc1] | $R^1$ = ethyl<br>$R^2$ = 2-phenylethyl<br>$R^3$ = hydrogen<br>$R^4$ = hydrogen<br>$R^5$ = 4-(N-hydroxyamino-carbonyl)benzyl<br>$R^6$ = hydrogen |
| 4c | 4-((2-ethyl-3,4-dihydro-4-oxo-3-phenethylquinazolin-8-yl)methyl)-N-hydroxybenzamide | 4c | $R^1$ = ethyl<br>$R^2$ = 2-phenylethyl<br>$R^3$ = hydrogen<br>$R^4$ = hydrogen<br>$R^5$ = hydrogen<br>$R^6$ = 4-(N-hydroxyamino-carbonyl)benzyl |
| 5a | 4-(2-ethyl-3,4-dihydro-4-oxo-3-phenethylquinazolin-8-yl)-N-hydroxybenzamide | 5a | $R^1$ = ethyl<br>$R^2$ = 2-phenylethyl<br>$R^3$ = hydrogen<br>$R^4$ = hydrogen<br>$R^5$ = hydrogen<br>$R^6$ = 4-(N-hydroxyamino-carbonyl)phenyl |

-continued

| Cpd No. | Chemical Name | Structure | Substituents of Formula X |
|---|---|---|---|
| 6a | (2E)-N-(2-aminophenyl)-3-(3,4-dihydro-2-methyl-4-oxo-3-phenethylquinazolin-7-yl)acrylamide | Formula (II) | $R^1$ = methyl<br>$R^2$ = 2-phenylethyl<br>$R^3$ = hydrogen<br>$R^4$ = hydrogen<br>$R^5$ = (2E)-3-N-(2-aminophenyl)-3-oxo-propenyl<br>$R^6$ = hydrogen |
| 2a | (2E)-3-(2-ethyl-6-fluoro-3,4-dihydro-4-oxo-3-phenethylquinazolin-7-yl)-N-hydroxyacrylamide | 2a<br>Formula (III) | $R^1$ = ethyl<br>$R^2$ = 2-phenylethyl<br>$R^3$ = hydrogen<br>$R^4$ = fluoro<br>$R^5$ = (2E)-3-N-hydroxyamino-3-oxo-propenyl<br>$R^6$ = hydrogen |
| 3a | (2E)-3-(2-ethyl-7-fluoro-3,4-dihydro-4-oxo-3-phenethylquinazolin-6-yl)-N-hydroxyacrylamide | 3a | $R^1$ = ethyl<br>$R^2$ = 2-phenylethyl<br>$R^3$ = hydrogen<br>$R^4$ = (2E)-3-N hydroxyamino-3-oxo-propenyl<br>$R^5$ = fluoro<br>$R^6$ = hydrogen |
| 3b | (2E)-3-(7-chloro-2-ethyl-3,4-dihydro-4-oxo-3-phenethylquinazolin-6-yl)-N-hydroxyacrylamide | 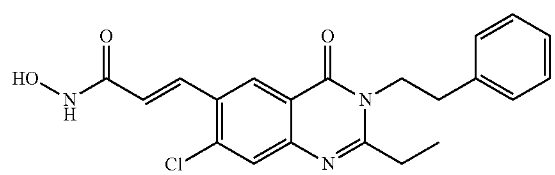 [SMILES: CCc1nc2cc(Cl)c(/C=C/C(=O)NO)cc2c(=O)n1CCc1ccccc1] | $R^1$ = ethyl<br>$R^2$ = 2-phenylethyl<br>$R^3$ = hydrogen<br>$R^4$ = (2E)-3-N hydroxyamino-3-oxo-propenyl<br>$R^5$ = chloro<br>$R^6$ = hydrogen |

$R^1$ is hydrogen, methyl, ethyl, cyclopropyl, or isopropyl;
$R^2$ is phenyl, benzyl, 2-phenylethyl, 3-phenylpropyl, 2-(1H-indol-3-yl)ethyl, 2-(4-fluorophenyl)ethyl, or 2-(4-methoxyphenyl)ethyl;
$R^3$ is hydrogen or (2E)-3-N-hydroxyamino-3-oxo-propenyl;
$R^4$ is hydrogen, fluoro, (2E)-3-N-hydroxyamino-3-oxo-propenyl, or 4-(N-hydroxyaminocarbonyl)benzyl;
$R^5$ is hydrogen, (2E)-3-N-hydroxyamino-3-oxo-propenyl, 4-(N-hydroxyaminocarbonyl)benzyl, or (2E)-3-N-(2-aminophenyl)-3-oxo-propenyl; and
$R^6$ is hydrogen, (2E)-3-N-hydroxyamino-3-oxo-propenyl, 4-(N-hydroxyaminocarbonyl)phenyl, or 4-(N-hydroxyaminocarbonyl)benzyl.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for inducing cytotoxicities in cancer cells associated with deregulation of the activity of histone deacetylases in a subject in need thereof, comprising:
administering to the subject in need thereof a compound of Formula X:

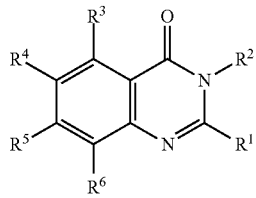

Formula X or a pharmaceutically acceptable salt thereof in a therapeutically effective amount to induce cytotoxicities in the cancer cells associated with deregulation of the activity of histone deacetylases, (I) wherein:
$R^1$ is hydrogen, $(C_1-C_6)$alkyl, or $(C_3-C_6)$cycloalkyl;
$R^2$ is $(C_6-C_{18})$aryl, $(C_6-C_{18})$aryl$(C_1-C_6)$alkyl, $(C_3-C_{18})$heteroaryl$(C_1-C_6)$alkyl, halo$(C_6-C_{18})$aryl$(C_1-C_6)$alkyl, or $(C_1-C_6)$alkoxy$(C_6-C_{18})$aryl$(C_1-C_6)$alkyl;
$R^3$ is N-hydroxyamino-oxo$(C_2-C_6)$alkenyl;
$R^4$ is hydrogen, halogen, N-hydroxyamino-oxo$(C_2-C_6)$alkenyl, or N-hydroxyaminocarbonyl$(C_6-C_{18})$aryl$(C_1-C_6)$alkylene;
$R^5$ is hydrogen, halogen, N-hydroxyamino-oxo$(C_2-C_6)$alkenyl, N-hydroxyaminocarbonyl$(C_6-C_{18})$aryl$(C_1-C_6)$alkylene, or amino$(C_6-C_{18})$aryl-oxo$(C_2-C_6)$alkenyl; and
$R^6$ is hydrogen, N-hydroxyamino-oxo$(C_2-C_6)$alkenyl, N-hydroxyamino$(C_6-C_{18})$aryl $(C_1-C_6)$alkylene, or N-hydroxyaminocarbonyl$(C_6-C_{18})$aryl$(C_1-C_6)$alkylene;

(II) or wherein:
$R^1$, $R^2$, $R^5$ and $R^6$ are each as defined in (I) above;
$R^3$ is hydrogen or N-hydroxyamino-oxo$(C_2-C_6)$alkenyl; and
$R^4$ is N-hydroxyamino-oxo$(C_2-C_6)$alkenyl, or N-hydroxyaminocarbonyl$(C_6-C_{18})$aryl$(C_1-C_6)$alkylene;

(III) or wherein:
$R^1$, $R^2$, $R^4$ and $R^6$ are each as defined in (I) above;
$R^3$ is as defined in (II) above; and
$R^5$ is N-hydroxyamino-oxo$(C_2-C_6)$alkenyl, N-hydroxyaminocarbonyl$(C_6-C_{18})$aryl$(C_1-C_6)$alkylene, or amino$(C_6-C_{18})$aryl-oxo$(C_2-C_6)$alkenyl;

(IV) or wherein:
$R^1$, $R^2$, $R^4$, $R^5$ are each as defined in (I) above;
$R^3$ is as defined in (II) above; and
$R^6$ is N-hydroxyamino-oxo$(C_2-C_6)$alkenyl, N-hydroxyamino$(C_6-C_{18})$aryl $(C_1-C_6)$alkylene, or N-hydroxyaminocarbonyl$(C_6-C_{18})$aryl$(C_1-C_6)$alkylene.

2. The method of claim 1,
(A) wherein:
$R^1$ is hydrogen, methyl, ethyl, cyclopropyl, or isopropyl;
$R^2$ is phenyl, benzyl, 2-phenylethyl, 3-phenylpropyl, 2-(1H-indol-3-yl)ethyl, 2-(4-fluorophenyl)ethyl, or 2-(4-methoxyphenyl)ethyl;
$R^3$ is (2E)-3-N-hydroxyamino-3-oxo-propenyl;
$R^4$ is hydrogen, fluoro, (2E)-3-N-hydroxyamino-3-oxo-propenyl, or 4-(N-hydroxyaminocarbonyl)benzyl;
$R^5$ is hydrogen, chloro, fluoro, (2E)-3-N-hydroxyamino-3-oxo-propenyl, 4-(N-hydroxyaminocarbonyl)benzyl, or (2E)-3-N-(2-aminophenyl)-3-oxo-propenyl; and
$R^6$ is hydrogen, (2E)-3-N-hydroxyamino-3-oxo-propenyl, 4-(N-hydroxyaminocarbonyl)phenyl, or 4-(N-hydroxyaminocarbonyl)benzyl, or a salt thereof;

(B) or wherein:
$R^1$, $R^2$, $R^5$ and $R^6$ are each as defined in (A) above;
$R^3$ is hydrogen or (2E)-3-N-hydroxyamino-3-oxo-propenyl; and
$R^4$ is (2E)-3-N-hydroxyamino-3-oxo-propenyl, or 4-(N-hydroxyaminocarbonyl)benzyl;

(C) or wherein:
$R^1$, $R^2$, $R^4$ and $R^6$ are each as defined in (A) above;
$R^3$ is as defined in (B) above; and
$R^5$ is (2E)-3-N-hydroxyamino-3-oxo-propenyl, 4-(N-hydroxyaminocarbonyl)benzyl, or (2E)-3-N-(2-aminophenyl)-3-oxo-propenyl;

(D) or wherein:
$R^1$, $R^2$, $R^4$ and $R^5$ are each as defined in (A) above;
$R^3$ is as defined in (B) above; and
$R^6$ is (2E)-3-N-hydroxyamino-3-oxo-propenyl, 4-(N-hydroxyaminocarbonyl)phenyl, or 4-(N-hydroxyaminocarbonyl)benzyl, or a salt thereof.

3. The method of claim 2,
(i) wherein:
$R^1$ is hydrogen, methyl, ethyl, cyclopropyl, or isopropyl;
$R^2$ is phenyl, benzyl, 2-phenylethyl, 3-phenylpropyl, 2-(1H-indol-3-yl)ethyl, 2-(4-fluorophenyl)ethyl, or 2-(4-methoxyphenyl)ethyl;
$R^3$ is (2E)-3-N-hydroxyamino-3-oxo-propenyl;
$R^4$ is hydrogen, (2E)-3-N-hydroxyamino-3-oxo-propenyl, or 4-(N-hydroxyaminocarbonyl)benzyl;
$R^5$ is hydrogen, (2E)-3-N-hydroxyamino-3-oxo-propenyl, 4-(N-hydroxyaminocarbonyl)benzyl, or (2E)-3-N-(2-aminophenyl)-3-oxo-propenyl; and
$R^6$ is hydrogen, (2E)-3-N-hydroxyamino-3-oxo-propenyl, 4-(N-hydroxyaminocarbonyl)phenyl, or 4-(N-hydroxyaminocarbonyl)benzyl, or a salt thereof;

(ii) or wherein:
$R^1$, $R^2$, $R^5$ and $R^6$ are each as defined in (i) above;
$R^3$ is hydrogen or (2E)-3-N-hydroxyamino-3-oxo-propenyl; and
$R^4$ is (2E)-3-N-hydroxyamino-3-oxo-propenyl, or 4-(N-hydroxyaminocarbonyl)benzyl;

(iii) or wherein:
$R^1$, $R^2$, $R^4$ and $R^6$ are each as defined in (i) above;
$R^3$ is as defined in (ii) above; and
$R^5$ is (2E)-3-N-hydroxyamino-3-oxo-propenyl, 4-(N-hydroxyaminocarbonyl)benzyl, or (2E)-3-N-(2-aminophenyl)-3-oxo-propenyl;

(iv) or wherein:
$R^1$, $R^2$, $R^4$ and $R^5$ are each as defined in (i) above;
$R^3$ is as defined in (ii) above; and
$R^6$ is (2E)-3-N-hydroxyamino-3-oxo-propenyl, 4-(N-hydroxyaminocarbonyl)phenyl, or 4-(N-hydroxyaminocarbonyl)benzyl, or a salt thereof.

4. The method of claim 2, wherein
$R^1$ is ethyl;
$R^2$ is 2-phenylethyl;
$R^3$ is hydrogen;
$R^4$ is fluoro;
$R^5$ is (2E)-3-N-hydroxyamino-3-oxo-propenyl; and
$R^6$ is hydrogen, or a salt thereof.

5. The method of claim 2, wherein
$R^1$ is ethyl;
$R^2$ is 2-phenylethyl;

$R^3$ is hydrogen;
$R^4$ is (2E)-3-N-hydroxyamino-3-oxo-propenyl;
$R^5$ is chloro or fluoro; and
$R^6$ is hydrogen, or a salt thereof.

6. The method of claim 2, wherein the compound is selected from the group consisting of
(2E)-3-(3,4-dihydro-2-methyl-4-oxo-3-phenylquinazolin-5-yl)-N-hydroxyacrylamide,
(2E)-3-(3,4-dihydro-2-methyl-4-oxo-3-phenylquinazolin-6-yl)-N-hydroxyacrylamide,
(2E)-3-(3,4-dihydro-2-methyl-4-oxo-3-phenylquinazolin-7-yl)-N-hydroxyacrylamide,
(2E)-3-(3,4-dihydro-2-methyl-4-oxo-3-phenylquinazolin-8-yl)-N-hydroxyacrylamide,
(2E)-3-(3-benzyl-3,4-dihydro-2-methyl-4-oxoquinazolin-7-yl)-N-hydroxyacrylamide,
(2E)-3-(3,4-dihydro-2-methyl-4-oxo-3-phenethylquinazolin-7-yl)-N-hydroxyacrylamide,
(2E)-3-(3-(2-(1H-indol-3-yl)ethyl)-3,4-dihydro-2-methyl-4-oxoquinazolin-7-yl)-N-hydroxyacrylamide,
(2E)-3-(3,4-dihydro-4-oxo-3-phenethylquinazolin-7-yl)-N-hydroxyacrylamide,
(2E)-3-(2-ethyl-3,4-dihydro-4-oxo-3-phenethylquinazolin-7-yl)-N-hydroxyacrylamide,
(2E)-3-(2-ethyl-3,4-dihydro-4-oxo-3-(3-phenylpropyl)quinazolin-7-yl)-N-hydroxyacrylamide,
(2E)-3-(2-cyclopropyl-3,4-dihydro-4-oxo-3-phenethylquinazolin-7-yl)-N-hydroxyacrylamide,
(2E)-3-(3,4-dihydro-2-isopropyl-4-oxo-3-phenethylquinazolin-7-yl)-N-hydroxyacrylamide,
(2E)-3-(3-(4-methoxyphenethyl)-2-ethyl-3,4-dihydro-4-oxoquinazolin-7-yl)-N-hydroxyacrylamide,
(2E)-3-(3-(4-fluorophenethyl)-2-ethyl-3,4-dihydro-4-oxoquinazolin-7-yl)-N-hydroxyacrylamide,
4-((2-ethyl-3,4-dihydro-4-oxo-3-phenethylquinazolin-6-yl)methyl)-N-hydroxybenzamide,
4-((2-ethyl-3,4-dihydro-4-oxo-3-phenethylquinazolin-7-yl)methyl)-N-hydroxy benzamide,
4-((2-ethyl-3,4-dihydro-4-oxo-3-phenethylquinazolin-8-yl)methyl)-N-hydroxy benzamide,
4-(2-ethyl-3,4-dihydro-4-oxo-3-phenethylquinazolin-8-yl)-N-hydroxybenzamide, and
(2E)-N-(2-aminophenyl)-3-(3,4-dihydro-2-methyl-4-oxo-3-phenethylquinazolin-7-yl)acrylamide.

7. The method of claim 2, wherein the compound is (2E)-3-(2-ethyl-6-fluoro-3,4-dihydro-4-oxo-3-phenethylquinazolin-7-yl)-N-hydroxyacrylamide, or a salt thereof.

8. The method of claim 2, wherein the compound is (2E)-3-(2-ethyl-7-fluoro-3,4-dihydro-4-oxo-3-phenethylquinazolin-6-yl)-N-hydroxyacrylamide, (2E)-3-(7-chloro-2-ethyl-3,4-dihydro-4-oxo-3-phenethylquinazolin-6-yl)-N-hydroxyacrylamide, or a salt thereof.

9. The method of claim 1, wherein the cancer is at least one selected from the group consisting of pancreatic carcinoma, hepatocellular carcinoma, colon tumor, breast tumor, prostate tumor, lymphoma and cutaneous tumor.

10. The method of claim 9, wherein the cutaneous tumor is at least one selected from the group consisting of melanomas and basal carcinomas.

11. The method of claim 1, wherein the cancer is at least one selected from the group consisting of breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, and acute lymphocytic leukemia.

12. A method for inhibiting growth of cancer cells in a patient having a cancer associated with deregulation of the activity of histone deacetylases, comprising:
administering to the patient a compound of Formula X:

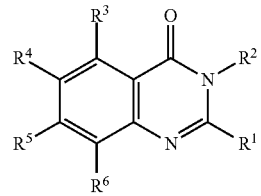

Formula X or a pharmaceutically acceptable salt thereof in a therapeutically effective amount to inhibit the growth of the cancer cells in the patient having a cancer associated with deregulation of the activity of histone deacetylases,
(I) wherein:
$R^1$ is hydrogen, $(C_1-C_6)$alkyl, or $(C_3-C_6)$cycloalkyl;
$R^2$ is $(C_6-C_{18})$aryl, $(C_6-C_{18})$aryl$(C_1-C_6)$alkyl, $(C_3-C_{18})$heteroaryl$(C_1-C_6)$alkyl, halo$(C_6-C_{18})$aryl$(C_1-C_6)$alkyl, or $(C_1-C_6)$alkoxy$(C_6-C_{18})$aryl$(C_1-C_6)$alkyl;
$R^3$ is N-hydroxyamino-oxo$(C_2-C_6)$alkenyl;
$R^4$ is hydrogen, halogen, N-hydroxyamino-oxo$(C_2-C_6)$alkenyl, or N-hydroxyaminocarbonyl$(C_6-C_{18})$aryl$(C_1-C_6)$alkylene;
$R^5$ is hydrogen, halogen, N-hydroxyamino-oxo$(C_2-C_6)$alkenyl, N-hydroxyaminocarbonyl$(C_6-C_{18})$aryl$(C_1-C_6)$alkylene, or amino$(C_6-C_{18})$aryl-oxo$(C_2-C_6)$alkenyl; and
$R^6$ is hydrogen, N-hydroxyamino-oxo$(C_2-C_6)$alkenyl, N-hydroxyamino$(C_6-C_{18})$aryl $(C_1-C_6)$alkylene, or N-hydroxyaminocarbonyl$(C_6-C_{18})$aryl$(C_1-C_6)$alkylene;
(II) or wherein:
$R^1$, $R^2$, $R^5$ and $R^6$ are each as defined in (I) above;
$R^3$ is hydrogen or N-hydroxyamino-oxo$(C_2-C_6)$alkenyl; and
$R^4$ is N-hydroxyamino-oxo$(C_2-C_6)$alkenyl, or N-hydroxyaminocarbonyl$(C_6-C_{18})$aryl$(C_1-C_6)$alkylene;
(III) or wherein:
$R^1$, $R^2$, $R^4$ and $R^6$ are each as defined in (I) above;
$R^3$ is as defined in (II) above; and
$R^5$ is N-hydroxyamino-oxo$(C_2-C_6)$alkenyl, N-hydroxyaminocarbonyl$(C_6-C_{18})$aryl$(C_1-C_6)$alkylene, or amino$(C_6-C_{18})$aryl-oxo$(C_2-C_6)$alkenyl;
(IV) or wherein:
$R^1$, $R^2$, $R^4$, $R^5$ are each as defined in (I) above;
$R^3$ is as defined in (II) above; and
$R^6$ is N-hydroxyamino-oxo$(C_2-C_6)$alkenyl, N-hydroxyamino$(C_6-C_{18})$aryl $(C_1-C_6)$alkylene, or N-hydroxyaminocarbonyl$(C_6-C_{18})$aryl$(C_1-C_6)$alkylene.

13. The method of claim 12,
(A) wherein:
$R^1$ is hydrogen, methyl, ethyl, cyclopropyl, or isopropyl;
$R^2$ is phenyl, benzyl, 2-phenylethyl, 3-phenylpropyl, 2-(1H-indol-3-yl)ethyl, 2-(4-fluorophenyl)ethyl, or 2-(4-methoxyphenyl)ethyl;
$R^3$ is (2E)-3-N-hydroxyamino-3-oxo-propenyl;
$R^4$ is hydrogen, fluoro, (2E)-3-N-hydroxyamino-3-oxo-propenyl, or 4-(N-hydroxyaminocarbonyl)benzyl;
$R^5$ is hydrogen, chloro, fluoro, (2E)-3-N-hydroxyamino-3-oxo-propenyl, 4-(N-hydroxyaminocarbonyl)benzyl, or (2E)-3-N-(2-aminophenyl)-3-oxo-propenyl; and R⁶ is hydrogen, (2E)-3-N-hydroxyamino-3-oxo-propenyl, 4-(N-hydroxyaminocarbonyl)phenyl, or 4-(N-hydroxyaminocarbonyl)benzyl, or a salt thereof;
(B) or wherein:
R¹, R², R⁵ and R⁶ are each as defined in (A) above;
R³ is hydrogen or (2E)-3-N-hydroxyamino-3-oxo-propenyl; and
R⁴ is (2E)-3-N-hydroxyamino-3-oxo-propenyl, or 4-(N-hydroxyaminocarbonyl)benzyl;
(C) or wherein:
R¹, R², R⁴ and R⁶ are each as defined in (A) above;
R³ is as defined in (B) above; and
R⁵ is (2E)-3-N-hydroxyamino-3-oxo-propenyl, 4-(N-hydroxyaminocarbonyl)benzyl, or (2E)-3-N-(2-aminophenyl)-3-oxo-propenyl;
(D) or wherein:
R¹, R², R⁴ and R⁵ are each as defined in (A) above;
R³ is as defined in (B) above; and
R⁶ is (2E)-3-N-hydroxyamino-3-oxo-propenyl, 4-(N-hydroxyaminocarbonyl)phenyl, or 4-(N-hydroxyaminocarbonyl)benzyl, or a salt thereof.

14. The method of claim 13,
(i) wherein:
R¹ is hydrogen, methyl, ethyl, cyclopropyl, or isopropyl;
R² is phenyl, benzyl, 2-phenylethyl, 3-phenylpropyl, 2-(1H-indol-3-yl)ethyl, 2-(4-fluorophenyl)ethyl, or 2-(4-methoxyphenyl)ethyl;
R³ is (2E)-3-N-hydroxyamino-3-oxo-propenyl;
R⁴ is hydrogen, (2E)-3-N-hydroxyamino-3-oxo-propenyl, or 4-(N-hydroxyaminocarbonyl)benzyl;
R⁵ is hydrogen, (2E)-3-N-hydroxyamino-3-oxo-propenyl, 4-(N-hydroxyaminocarbonyl)benzyl, or (2E)-3-N-(2-aminophenyl)-3-oxo-propenyl; and
R⁶ is hydrogen, (2E)-3-N-hydroxyamino-3-oxo-propenyl, 4-(N-hydroxyaminocarbonyl)phenyl, or 4-(N-hydroxyaminocarbonyl)benzyl, or a salt thereof;
(ii) or wherein:
R¹, R², R⁵ and R⁶ are each as defined in (i) above;
R³ is hydrogen or (2E)-3-N-hydroxyamino-3-oxo-propenyl; and
R⁴ is (2E)-3-N-hydroxyamino-3-oxo-3-oxo-propenyl, or 4-(N-hydroxyaminocarbonyl)benzyl;
(iii) or wherein:
R¹, R², R⁵ and R⁶ are each as defined in (i) above;
R³ is as defined in (ii) above; and
R⁵ is (2E)-3-N-hydroxyamino-3-oxo-propenyl, 4-(N-hydroxyaminocarbonyl)benzyl, or (2E)-3-N-(2-aminophenyl)-3-oxo-propenyl;
(iv) or wherein:
R¹, R², R⁴ and R⁵ are each as defined in (i) above;
R³ is as defined in (ii) above; and
R⁶ is (2E)-3-N-hydroxyamino-3-oxo-propenyl, 4-(N-hydroxyaminocarbonyl)phenyl, or 4-(N-hydroxyaminocarbonyl)benzyl, or a salt thereof.

15. The method of claim 13, wherein
R¹ is ethyl;
R² is 2-phenylethyl;
R³ is hydrogen;
R⁴ is fluoro;
R⁵ is (2E)-3-N-hydroxyamino-3-oxo-propenyl; and
R⁶ is hydrogen, or a salt thereof.

16. The method of claim 13, wherein
R¹ is ethyl;
R² is 2-phenylethyl;
R³ is hydrogen;
R⁴ is (2E)-3-N-hydroxyamino-3-oxo-propenyl;
R⁵ is chloro or fluoro; and
R⁶ is hydrogen, or a salt thereof.

17. The method of claim 13, wherein the compound is selected from the group consisting of
(2E)-3-(3,4-dihydro-2-methyl-4-oxo-3-phenylquinazolin-5-yl)-N-hydroxyacrylamide,
(2E)-3-(3,4-dihydro-2-methyl-4-oxo-3-phenylquinazolin-6-yl)-N-hydroxyacrylamide,
(2E)-3-(3,4-dihydro-2-methyl-4-oxo-3-phenylquinazolin-7-yl)-N-hydroxyacrylamide,
(2E)-3-(3,4-dihydro-2-methyl-4-oxo-3-phenylquinazolin-8-yl)-N-hydroxyacrylamide,
(2E)-3-(3-benzyl-3,4-dihydro-2-methyl-4-oxoquinazolin-7-yl)-N-hydroxyacrylamide,
(2E)-3-(3,4-dihydro-2-methyl-4-oxo-3-phenethylquinazolin-7-yl)-N-hydroxyacrylamide,
(2E)-3-(3-(2-(1H-indol-3-yl)ethyl)-3,4-dihydro-2-methyl-4-oxoquinazolin-7-yl)-N-hydroxyacrylamide,
(2E)-3-(3,4-dihydro-4-oxo-3-phenethylquinazolin-7-yl)-N-hydroxyacrylamide,
(2E)-3-(2-ethyl-3,4-dihydro-4-oxo-3-phenethylquinazolin-7-yl)-N-hydroxyacrylamide,
(2E)-3-(2-ethyl-3,4-dihydro-4-oxo-3-(3-phenylpropyl)quinazolin-7-yl)-N-hydroxyacrylamide,
(2E)-3-(2-cyclopropyl-3,4-dihydro-4-oxo-3-phenethylquinazolin-7-yl)-N-hydroxyacrylamide,
(2E)-3-(3,4-dihydro-2-isopropyl-4-oxo-3-phenethylquinazolin-7-yl)-N-hydroxyacrylamide,
(2E)-3-(3-(4-methoxyphenethyl)-2-ethyl-3,4-dihydro-4-oxoquinazolin-7-yl)-N-hydroxyacrylamide,
(2E)-3-(3-(4-fluorophenethyl)-2-ethyl-3,4-dihydro-4-oxoquinazolin-7-yl)-N-hydroxyacrylamide,
4-((2-ethyl-3,4-dihydro-4-oxo-3-phenethylquinazolin-6-yl)methyl)-N-hydroxybenzamide,
4-((2-ethyl-3,4-dihydro-4-oxo-3-phenethylquinazolin-7-yl)methyl)-N-hydroxybenzamide,
4-((2-ethyl-3,4-dihydro-4-oxo-3-phenethylquinazolin-8-yl)methyl)-N-hydroxybenzamide,
4-(2-ethyl-3,4-dihydro-4-oxo-3-phenethylquinazolin-8-yl)-N-hydroxybenzamide and
(2E)-N-(2-aminophenyl)-3-(3,4-dihydro-2-methyl-4-oxo-3-phenethylquinazolin-7-yl)acrylamide.

18. The method of claim 13, wherein the compound is (2E)-3-(2-ethyl-6-fluoro-3,4-dihydro-4-oxo-3-phenethylquinazolin-7-yl)-N-hydroxyacrylamide, or a salt thereof.

19. The method of claim 13, wherein the compound is (2E)-3-(2-ethyl-7-fluoro-3,4-dihydro-4-oxo-3-phenethylquinazolin-6-yl)-N-hydroxyacrylamide, (2E)-3-(7-chloro-2-ethyl-3,4-dihydro-4-oxo-3-phenethylquinazolin-6-yl)-N-hydroxyacrylamide, or a salt thereof.

20. The method of claim 13, wherein the cancer is selected from the group consisting of lung adenocarcinoma, colorectal cancer, pancreatic carcinoma, and hepatocellular carcinoma.

* * * * *